US010436697B2

(12) United States Patent
Vrane

(10) Patent No.: US 10,436,697 B2
(45) Date of Patent: Oct. 8, 2019

(54) FLOW CYTOMETERY SYSTEM WITH FLUIDICS CONTROL SYSTEM

(71) Applicant: CYTEK BIOSCIENCES, INC., Fremont, CA (US)

(72) Inventor: David Vrane, San Jose, CA (US)

(73) Assignee: Cytek Biosciences, Inc., Fremont, CA (US)

( * ) Notice: Subject to any disclaimer, the term of this patent is extended or adjusted under 35 U.S.C. 154(b) by 0 days.

(21) Appl. No.: 15/817,237

(22) Filed: Nov. 19, 2017

(65) Prior Publication Data

US 2018/0156710 A1 Jun. 7, 2018

Related U.S. Application Data

(60) Provisional application No. 62/424,464, filed on Nov. 19, 2016.

(51) Int. Cl.
*G01N 15/10* (2006.01)
*G01N 15/14* (2006.01)
*G01N 21/49* (2006.01)

(52) U.S. Cl.
CPC ....... *G01N 15/1404* (2013.01); *G01N 15/147* (2013.01); *G01N 15/1434* (2013.01); *G01N 15/1436* (2013.01); *G01N 21/49* (2013.01); *G01N 2015/1006* (2013.01); *G01N 2015/1075* (2013.01); *G01N 2015/1409* (2013.01); *G01N 2015/1438* (2013.01)

(58) Field of Classification Search
CPC .................. G01N 21/47; G01N 21/49; G01N 2021/4704; G01N 2021/4707; G01N 2021/4709; G01N 2021/4711; G01N 2021/4733; G01N 15/1404; G01N 15/147; G01N 15/1434; G01N 15/1436; G01N 2014/1006; G01N 2014/1438; G01N 2014/1409; G01N 2014/10755
USPC .................................................. 356/337–343
See application file for complete search history.

(56) References Cited

U.S. PATENT DOCUMENTS

| | | | | |
|---|---|---|---|---|
| 3,916,197 A | * | 10/1975 | Fulwyler | G01N 15/1434 250/304 |
| 4,573,796 A | * | 3/1986 | Martin | G01N 15/1429 250/461.2 |
| 4,987,539 A | | 1/1991 | Moore et al. | |
| 5,483,469 A | | 1/1996 | Van den Engh et al. | |
| 5,760,900 A | * | 6/1998 | Ito | G01N 15/1434 250/461.2 |
| 6,767,188 B2 | | 7/2004 | Vrane et al. | |
| 7,544,326 B2 | | 6/2009 | Norton et al. | |

(Continued)

OTHER PUBLICATIONS

Young, Lee W.; PCT/US17/62444, International Search Report and Opinion; dated Mar. 28, 2018, 11 pages.

*Primary Examiner* — Gordon J Stock, Jr.
(74) *Attorney, Agent, or Firm* — Alford Law Group, Inc.; Tobi C. Clinton; William E. Alford

(57) ABSTRACT

A system, method, and apparatus are provided for flow cytometry. In one example, the flow cytometry system includes dual laser devices and dual scatter channels to measure velocity of particles in a core stream of sample fluid. The total flow rate of the sample fluid and the sheath fluid around the sample fluid is controlled, and thus held constant, by a feedback control system controlling a vacuum pump based on differential pressure across ends of a flow channel in the flow cell.

18 Claims, 14 Drawing Sheets

(56) References Cited

U.S. PATENT DOCUMENTS

| | | |
|---|---|---|
| 7,880,108 B2 | 2/2011 | Schembri et al. |
| 9,575,050 B2 | 2/2017 | Vrane et al. |
| 2003/0162304 A1 | 8/2003 | Dority et al. |
| 2004/0027914 A1 | 2/2004 | Vrane |
| 2004/0042930 A1 | 3/2004 | Clemens et al. |
| 2005/0243307 A1* | 11/2005 | Silcott ................ G01N 15/1459 356/73 |
| 2008/0291425 A1 | 11/2008 | Norton et al. |
| 2011/0134426 A1 | 6/2011 | Kaduchak et al. |
| 2012/0070818 A1* | 3/2012 | Rowlen .............. G01N 15/1404 435/3 |
| 2012/0103112 A1* | 5/2012 | Vrane ................ G01N 15/1404 73/864.35 |
| 2015/0115174 A1 | 4/2015 | Chen |
| 2015/0140577 A1 | 5/2015 | Li |
| 2015/0330385 A1 | 11/2015 | Lofstrom et al. |
| 2017/0307505 A1 | 10/2017 | Vrane et al. |
| 2018/0024040 A1 | 1/2018 | Yan et al. |
| 2018/0156711 A1* | 6/2018 | Vrane ................ G01N 15/1459 |

\* cited by examiner

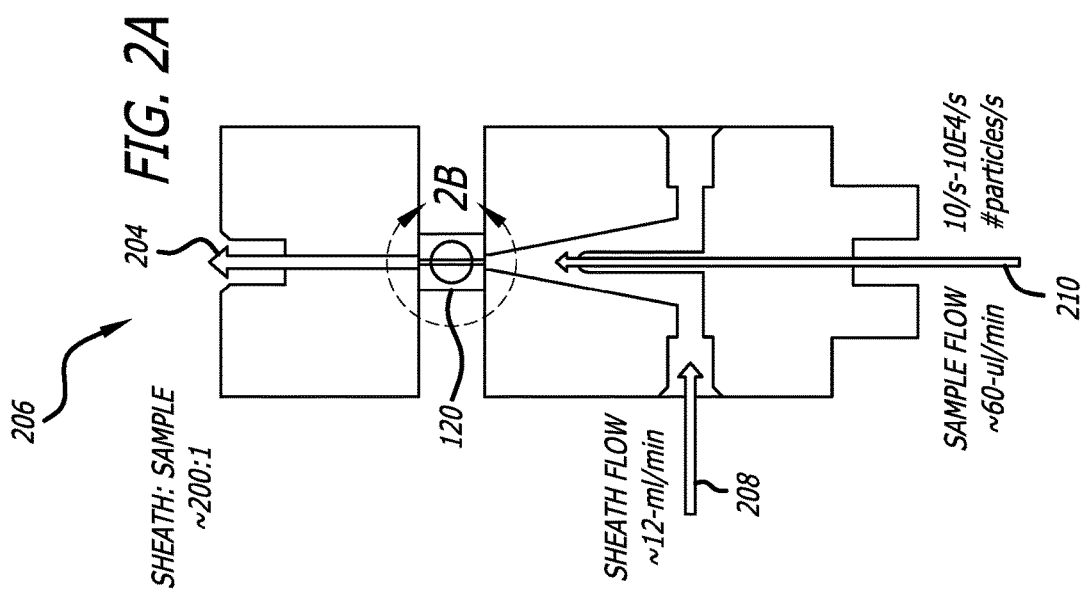

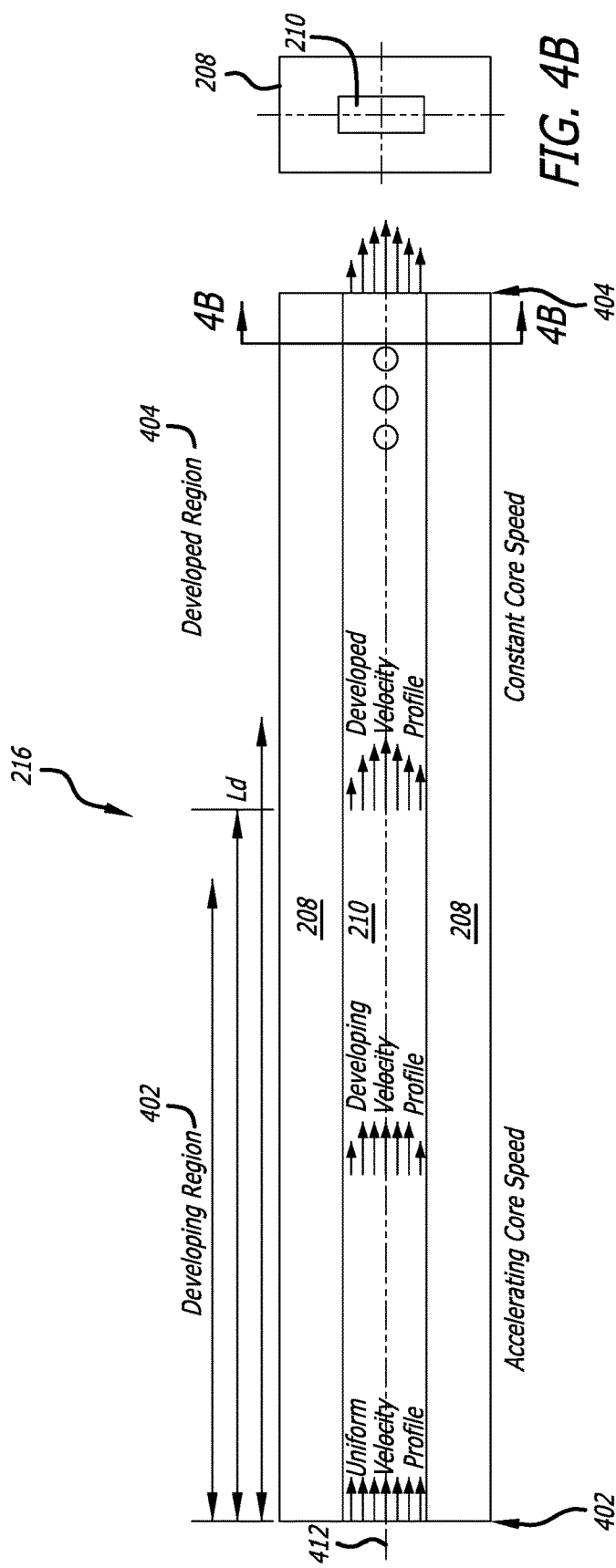

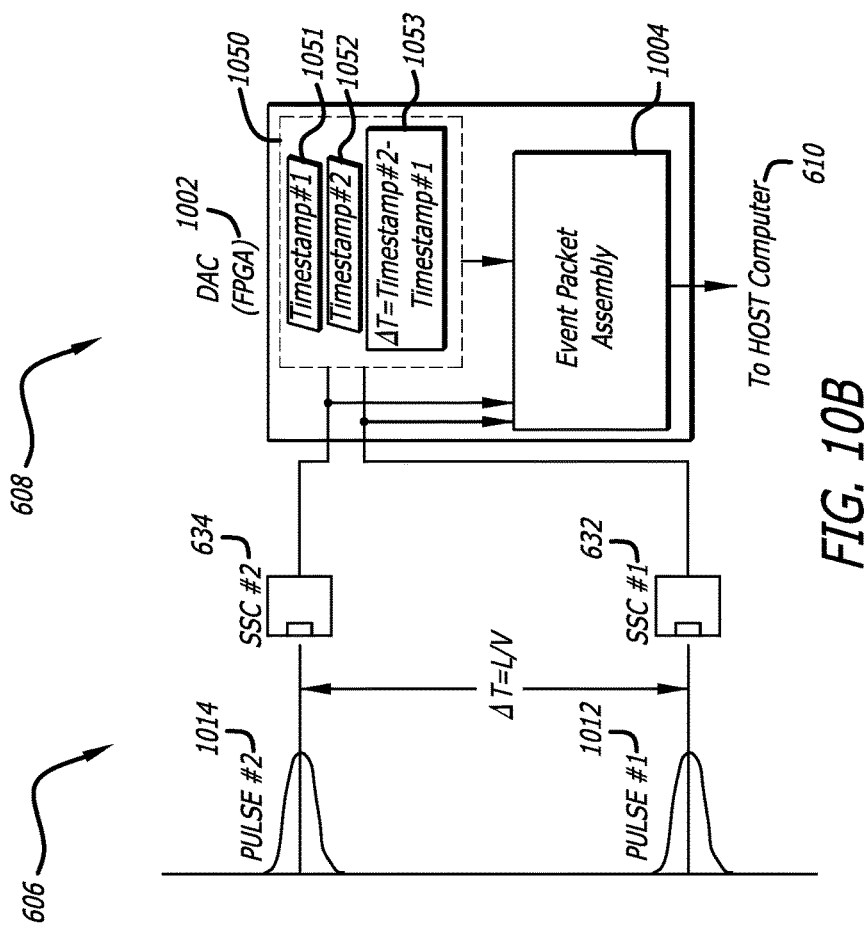
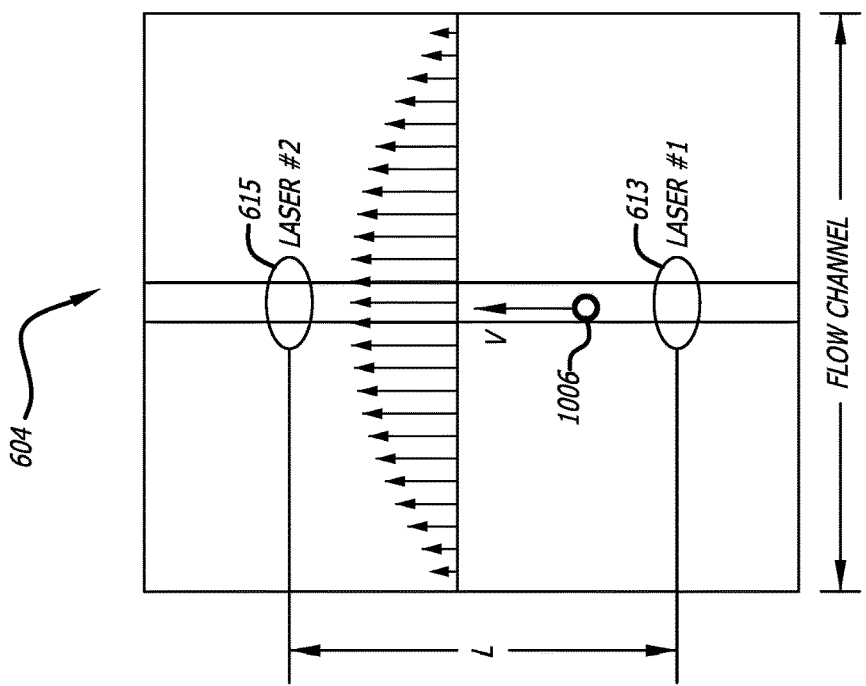
FIG. 10A
FIG. 10B

FLOW CYTOMETERY SYSTEM WITH FLUIDICS CONTROL SYSTEM

CROSS REFERENCE TO RELATED APPLICATION

This patent application claims the benefit of U.S. Provisional Patent Application No. 62/424,464 titled FLOW CYTOMETRY SYSTEM AND STEPPER MOTOR PINCH VALVE THEREFOR filed on Nov. 19, 2016 by inventors David Vrane et al.

FIELD

The embodiments of the invention relate generally to flow cytometry systems.

BACKGROUND

Flow cytometry involves the optical measurement of cells or particles of a test sample carried in a fluid flow. The collective instrumentation that achieves this task is known as a flow cytometer.

The control of the flow fluid with the test sample in a flow cytometer is important to accurately analyze the type and quantity of cells or particles in the test sample. If the velocity of the fluid flow is a variable (e.g., too low or high around a typical), the identity of cells or particles in the test sample can be misrepresented. Moreover, an overcomplicated fluid control system may be unreliable with extra control devices.

Accordingly, it is desirable to improve upon flow control systems in flow cytometers.

BRIEF SUMMARY

The embodiments are summarized by the claims. However, briefly, a system, method, and apparatus for flow cytometry fluidics in a flow cytometer are described.

A flow cytometry system includes dual laser devices and dual scatter channels to measure velocity of particles in a core stream of sample fluid. A first scatter channel detects a first light scatter generated by a particle passing through a first laser beam, wherein the particle flows in a sample fluid. A second scatter channel detects a second light scatter generated by the particle passing through a second laser beam, wherein the first laser beam and the second laser beam are separated by a distance (L).

The flow cytometry system also includes a stepper motor modulated valve to control the proportion of sheath flow rate and sample flow rate in a flow channel. The total flow rate of the sample fluid and sheath fluid around the sample fluid is controlled, and thus held constant, by a feedback control system controlling a vacuum pump based on differential pressure across a flow channel in the flow cell. Particle velocity in the flow channel is a function of the total flow rate.

BRIEF DESCRIPTIONS OF THE DRAWINGS

Various embodiments are illustrated by way of example, and not by way of limitation, in the figures of the accompanying drawings.

FIG. 2A is a schematic diagram of an example flow cell, such as that which is included in the fluidics system of FIG. 1.

FIG. 2B is a magnified view of the fluid flow in a flow channel for the flow cell shown in FIG. 2A.

FIG. 4A is a conceptual diagram illustrating flow development within a flow channel.

FIG. 4B is a diagram illustrating a cross-sectional view of the flow channel shown in FIG. 4A.

FIG. 10A is a block diagram showing additional details of the fluidics system in relation to emission optics.

FIG. 10B is a block diagram showing more details of the acquisition system in relation to FIG. 10A.

It will be recognized that some or all of the Figures are for purposes of illustration and do not necessarily depict the actual relative sizes or locations of the elements shown. The Figures are provided for the purpose of illustrating one or more embodiments with the explicit understanding that they will not be used to limit the scope or the meaning of the claims.

DETAILED DESCRIPTION

In the following detailed description of the embodiments, numerous specific details are set forth. However, it will be obvious to one skilled in the art that the embodiments may be practiced without these specific details. In other instances well known methods, procedures, components, and circuits have not been described in detail so as not to unnecessarily obscure aspects of the embodiments.

A system, method, and apparatus are provided for flow cytometry fluidics. The system includes dual laser devices and dual scatter channels to measure time differences and calculate velocity of particles in a core stream of sample fluid. The system also includes a stepper motor modulated flow control valve to control the proportion of sheath flow rate and sample flow rate in a flow channel. The total flow rate of the sample fluid and the sheath fluid around the sample fluid is controlled, and thus held constant, by a feedback control system controlling a vacuum pump based on differential pressure across a flow channel in the flow cell. Details of the system, method, and apparatus are further described with reference to the figures.

Scattered light off of a particle is not a fluorescent light emitted by a marker attached to the particle. Dual side scatter channels (SSC) are mentioned herein as receiving scattered light off a particle that flows through a laser beam. However, scattered light may be received off a particle at many angles. The dual side scatter channels (SSC) mentioned herein may instead be off angle scatter channels, forward scatter channels, back scatter channels, or combinations thereof that receive scattered light off a particle at various angles. Accordingly, the various devices for collecting scattered light at various angles are collectively and more broadly referred to herein as scatter channels.

General Overview

Figure 1:
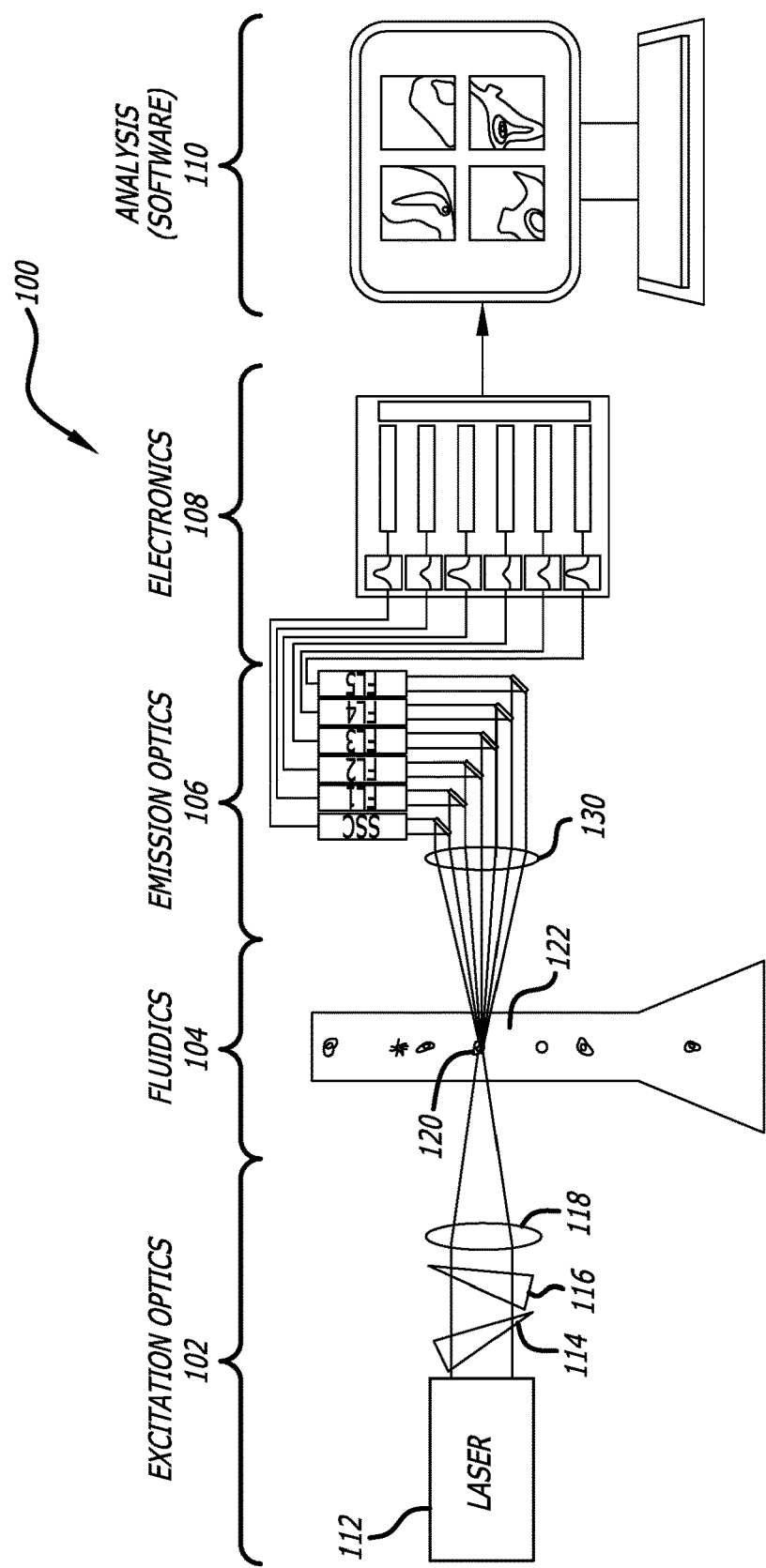
FIG. 1 is a basic conceptual diagram of a flow cytometer system.

FIG. 1 is a basic conceptual diagram of a flow cytometer system 100. Five major subsystems of the flow cytometer system 100 include an excitation optics system 102, a fluidics system 104, an emission optics system 106, an acquisition system 108, and an analysis system 110. Generally, a "system" includes hardware devices, software devices, or a combination thereof.

The excitation optics system 102 includes, for example, a laser device 112, an optical element 114, an optical element 116, and an optical element, 118. Example optical elements include an optical prism and an optical lens. The excitation optics system 102 illuminates an optical interrogation region 120. The fluidics system 104 carries fluid samples 122 through the optical interrogation region 120. The emission optics system 106 includes, for example, an optical element 130 and optical detectors SSC, FL1, FL2, FL3, FL4, and FL5. The emission optics system 106 gathers photons emitted or scattered from passing particles. The emission optics system 106 focuses these photons onto the optical detectors SSC, FL1, FL2, FL3, FL4, and FL5. Optical detector SSC is a side scatter channel. Optical detectors FL1, FL2, FL3, FL4, and FL5 are fluorescent detectors may include band-pass, or long-pass, filters to detect a particular fluorescence wavelength. Each optical detector converts photons into electrical pulses and sends the electrical pulses to the acquisition system 108. The acquisition system 108 processes and prepares these signals for analysis in the analysis system 110. Various embodiments of the flow cytometer 100 may be commercially available.

FIG. 2A is a schematic diagram of an example flow cell 206, which is included in the fluidics system 104 of FIG. 1. Given the importance of the flow cell 206 to the flow cytometry system 100, an understanding of its intended functions enables practical consideration of ways to improve flow cytometer performance.

The flow cell 206 provides important fluid dynamic and optical conditions that enable the optical excitation and collection of emitted light from individual cells passing serially through the interrogation region 120. In a simple representation shown in FIG. 2B, the flow cell 206 has a transparent flow channel 216 through which sheath fluid 208 and sample fluid 210 pass. In a portion of the transparent flow channel 216, the laser beam from the laser strikes particles in the sample fluid 210. The scattered light off the particles and/or fluorescent light from a marker attached to the particles is collected by one or more optical light sensors.

The following are ideal conditions in the flow channel 216: (a) the sample fluid 210 is surrounded by the sheath fluid 208 to form a core-annular flow of the sample fluid 210, and (b) the stream of sample fluid 210 is perfectly centered on the axis of the flow channel 204. If conditions (a) and (b) are met, and the sheath-to-sample volume ratio is sufficiently high, then particles within the core of the sample fluid 210 will (c) pass through the flow cell 206 in single file. For example, the core stream width 220 is sufficiently narrow (e.g., 20 micrometers) to enable particles flowing in single file. The sheath fluid 208 helps control core stream velocity 222 of the sample fluid 210. The latter condition (c) ensures that each particle receives exclusive illumination within the optical interrogation region 120. The process of achieving these flow conditions is called hydrodynamic focusing of the core of the sample fluid 210.

Hydrodynamic focusing is typically achieved by injecting the sample fluid 210 into the center of the sheath flow 208 at a wide cross section and then reducing the cross section to convectively stretch the combined flow. Hydrodynamic focusing differs from acoustic focusing. Acoustic focusing forces particles to the center of the channel by means of standing waves such as described in U.S. Pat. App. Pub. No. 2014/0147860 titled ACOUSTIC CYTOMETRY METHODS AND PROTOCOLS filed by Kaduchak et al. on Jun. 27, 2012.

While hydrodynamic focusing can provide the conditions to ensure interrogation of individual particles, hydrodynamic focusing does not guarantee measurements made on successive particles will be comparable. To produce comparable results, given two identical particles, the system must produce substantially identical optical outputs among particles. These optical outputs are in the form of a pulse.

Figure 3B:
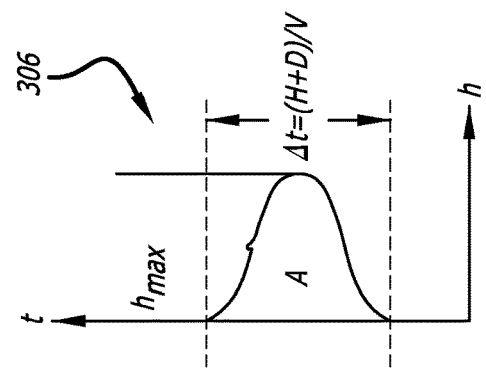
FIG. 3B is a graph showing characteristics of the optical pulse formed by the interaction between the particle and a laser beam shown in FIG. 3A.
Figure 3A:
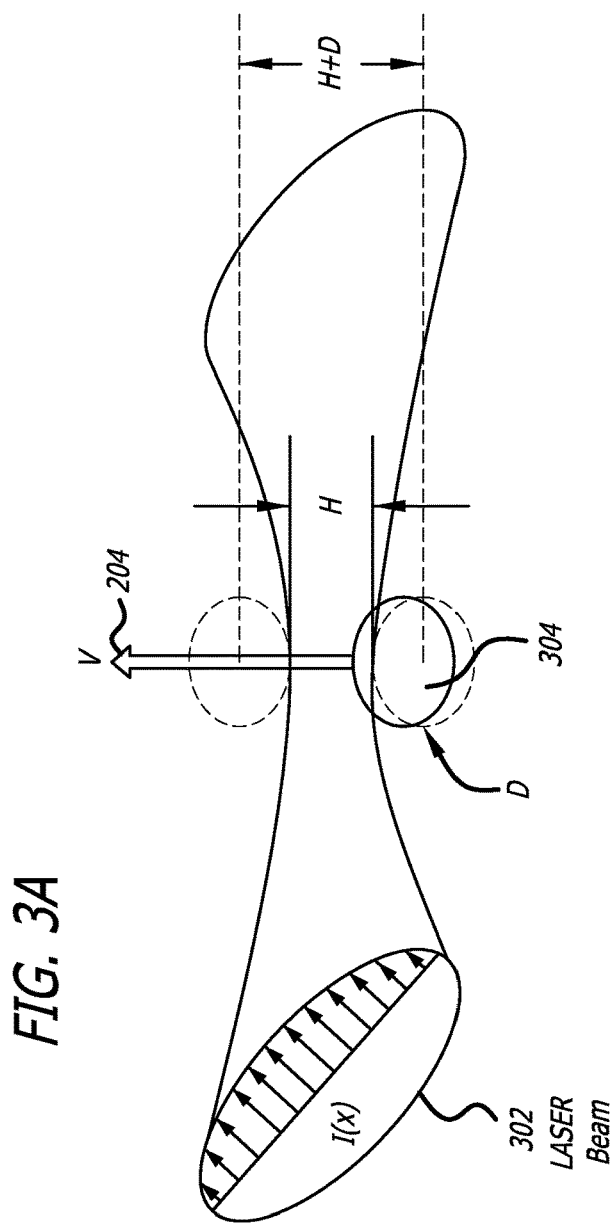
FIG. 3A is a conceptual diagram of an interaction between a particle and a laser beam to form an optical pulse.

FIG. 3A depicts a conceptual diagram of an interaction between a particle 304 and a laser beam 302 to form an optical pulse 306 shown in the graph of FIG. 3B. In the graph shown in FIG. 3B, the amplitude (A) of the optical pulse 306 depends on the excitation power and the emission characteristics of the particle 304 (e.g., size, shape, number of dye molecules, etc.). However, the width, or duration Δt, of the optical pulse 306 depends essentially on the diameter (D) of the particle 304, the height (H) of the excitation beam 302, and the velocity (V) of the particle 304. This pulse-width relationship may be given by the following equation:

$$\Delta t = \frac{D + H}{V} \quad \text{(Equation 1)}$$

where,
Δt=pulse width (e.g., microseconds),
D=particle diameter (e.g., micrometers),
H=beam height (e.g., micrometers), and
V=particle velocity (e.g., micrometers/microseconds).

Accordingly, two identical pulses travelling through the sample beam must have substantially the same velocity to produce the same pulse width. The particle velocity (V) at the interrogation region 120 (or interrogation point) is essentially determined by the flow behavior in the channel. As a consequence, the job of the fluidics 104 is essentially reduced to ensuring that particle velocities remain as consistent as possible.

Referring back to FIGS. 2A-2B, the fluidics system 104 is responsible for supplying sheath fluid 208 and sample fluid 210 to the flow cell 206. The sheath flow rate dominates the flow behavior in the flow cell 206 since it is typically many times greater than the sample flow rate. As a result, the sheath flow rate dominates the behavior of velocity inside the channel and is the most important factor in determining particle velocity 222. The sample flow rate controls the width 220 of the core stream. This is also important as it controls the potential range of positions that a given particle may take along the velocity profile in the channel.

The velocity profile 212 inside the channel depends on several factors with respect to classical fluid dynamics. The convective region of the flow cell hydrodynamically focuses the core-annular flow to stretch the sample stream until particles are (ideally) lined up one after another. Again, this is accomplished by accelerating the sample flow 210 through a reducing cross section width 220. Beyond the convective region, the cross sectional area of the flow remains constant. The flow enters this constant cross section channel at the inlet 401 with a uniform velocity profile whose magnitude equals flow rate divided by the cross sectional area of the flow, as represented by the following equation:

$$\overline{U} = \dot{Q}/A \qquad \text{(Equation 2)}$$

where,
$\overline{U}$=magnitude of uniform velocity profile
$\dot{Q}$=flow rate
A=cross sectional area of flow FIG. 4A is a conceptual diagram illustrating flow development within a flow channel 216. The flow channel includes, without limitation, an inlet 401, an outlet 404, and a center axis 412. As the flow travels down the flow channel 216, viscous drag of the walls 214 slows adjacent water molecules. To maintain constant flow rate (e.g., to conserve mass), water molecules in the center of the flow channel 216 must accelerate to compensate for the slowing particles near the walls 214. This communication of viscous drag through the fluid bulk continues until viscous forces precisely balance the driving axial pressure gradient. Up until this balance, the sample core stream 210 continues to accelerate. For rectangular channels with near-unity aspect ratios, such as shown by FIG. 4B, the terminal velocity of the sample core stream 210 is approximately twice the initial uniform velocity at the channel inlet 401.

The sample core stream 210 approaches terminal velocity within a developing region 402. Within the developing region 402, the core stream accelerates. The development length ($L_d$) is the physical distance required for the core stream 210 to achieve terminal velocity from the inlet 401. As described, development length ($L_d$) depends on viscosity. Viscosity is highly dependent on temperature. Higher temperatures result in longer development lengths ($L_d$).

Beyond the development length ($L_d$), in a developed region 404, the core stream velocity in the flow channel 216 does not change with distance, and the flow is considered "fully developed". Fully developed flow can also be independent of temperature. However, this requires that the total flow rate through the flow channel 216 remains constant. The consequence of flow development is that the velocity profile progresses from uniform (uniform velocity profile) at the channel inlet 401 to fully parabolic (developed velocity profile) at the development length ($L_d$).

With regard to flow cytometry, several important guidelines result from knowledge of channel flow fluid dynamics. As a first guideline, if the total flow rate through the flow channel 216 changes, then core stream velocity 222 will change. Hence, particle pulse widths (e.g., durations Δt) will change. Thus, flow rate variations should be minimized to ensure maximum system performance.

As a second guideline, the maximum velocity occurs along the axis 412 of the flow channel. Hence, any particle off of the axis 412 will have a slower velocity than particles on, or closer to, the axis 412. This means that identical particles will have different pulse widths (e.g., durations Δt) just by virtue of their position in the core stream. Thus, reducing core stream width 220 (e.g., reducing sample flow rate) minimizes pulse width variations due to the velocity profile.

As a third guideline, along the channel axis 412, the velocity is increasing by a factor of two in the developing region 402, and the length of the developing region 402 is dependent on temperature. Hence, if the interrogation region (or interrogation point) 120 resides in the developing region 402, the pulse widths (e.g., durations Δt) will change with temperature. Beyond the developing length ($L_d$), core stream velocity does not change with distance along the channel.

Figure 5:
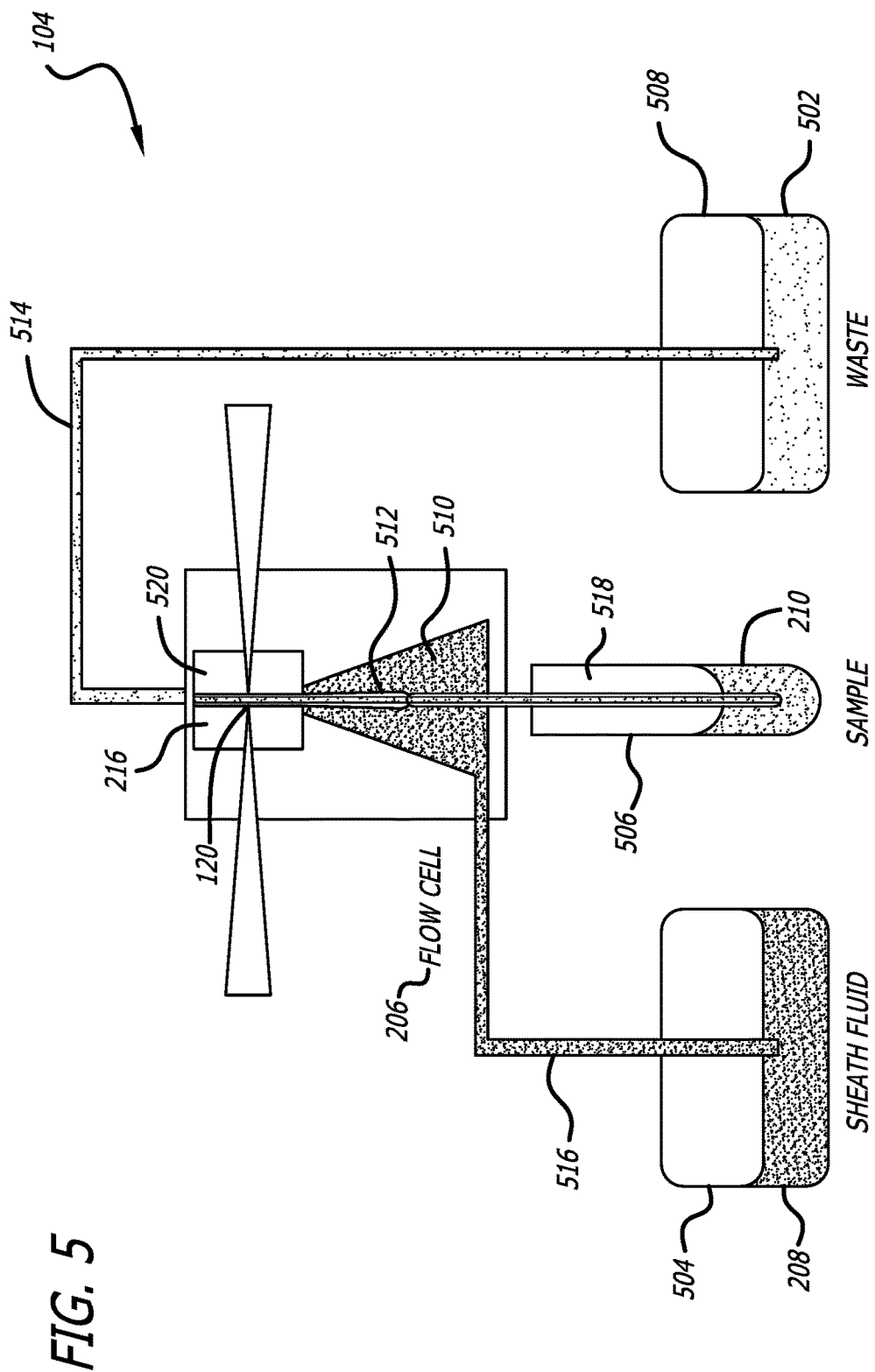
FIG. 5 is a basic conceptual diagram of the fluidics system of FIG. 1.

FIG. 5 is a basic conceptual diagram of the fluidics system 104 of FIG. 1. A fundamental goal of the fluidics system 104 is to provide sheath and sample to the flow cell 206 of FIG. 2. FIG. 5 shows the basic elements associated with this objective. A sheath straw 516 (e.g., tube) is inserted into the plenum tank 504. The fluidics system 104 supplies sheath fluid 208 from a sheath tank 626. The fluidics system 104 typically draws sample fluid 210 from a standard laboratory vessel 506. A sample straw 518 (e.g., tube) is inserted into the sample vessel 506. The fluidics system 104 injects the sample fluid 210 into the core 510 of the sheath flow 208 at the inlet to a contraction region 512 before the combined flows enter the flow channel/viewing orifice 520. Upon exit from the flow channel 216 at the outlet 404, the combined flows are routed to waste 502 in a waste container 508. Various commercial embodiments attempt to satisfy these fluidics objectives.

Flow Cytometry System

Despite various commercially available flow cytometry systems, there remains a need for a flow cytometry system that provides a flexible, yet relatively simple and reliable design, capable of accessing a wide array of sample vessel types, while offering uncompromised stability over a wide range of operating conditions.

Accordingly, a flow cytometry system is provided that includes dual laser devices and dual scatter channels (e.g., dual side scatter channels—SSC) to measure velocity of particles in a core stream of sample fluid. Typical systems measure pressure and then use that measured pressure to maintain constant pressure and velocity in the system; unfortunately, that is an indirect way of controlling velocity of sample particles. The system also includes a stepper motor modulated flow control valve to control the proportion of sheath flow rate and sample flow rate in a flow channel. The total flow rate of the sample fluid and the sheath fluid around the sample fluid is controlled, and thus held constant, by a feedback control system controlling a vacuum pump based on differential pressure across a flow channel in the flow cell. Details of the system, method, and apparatus are further described with reference to the Figures.

Figure 6:
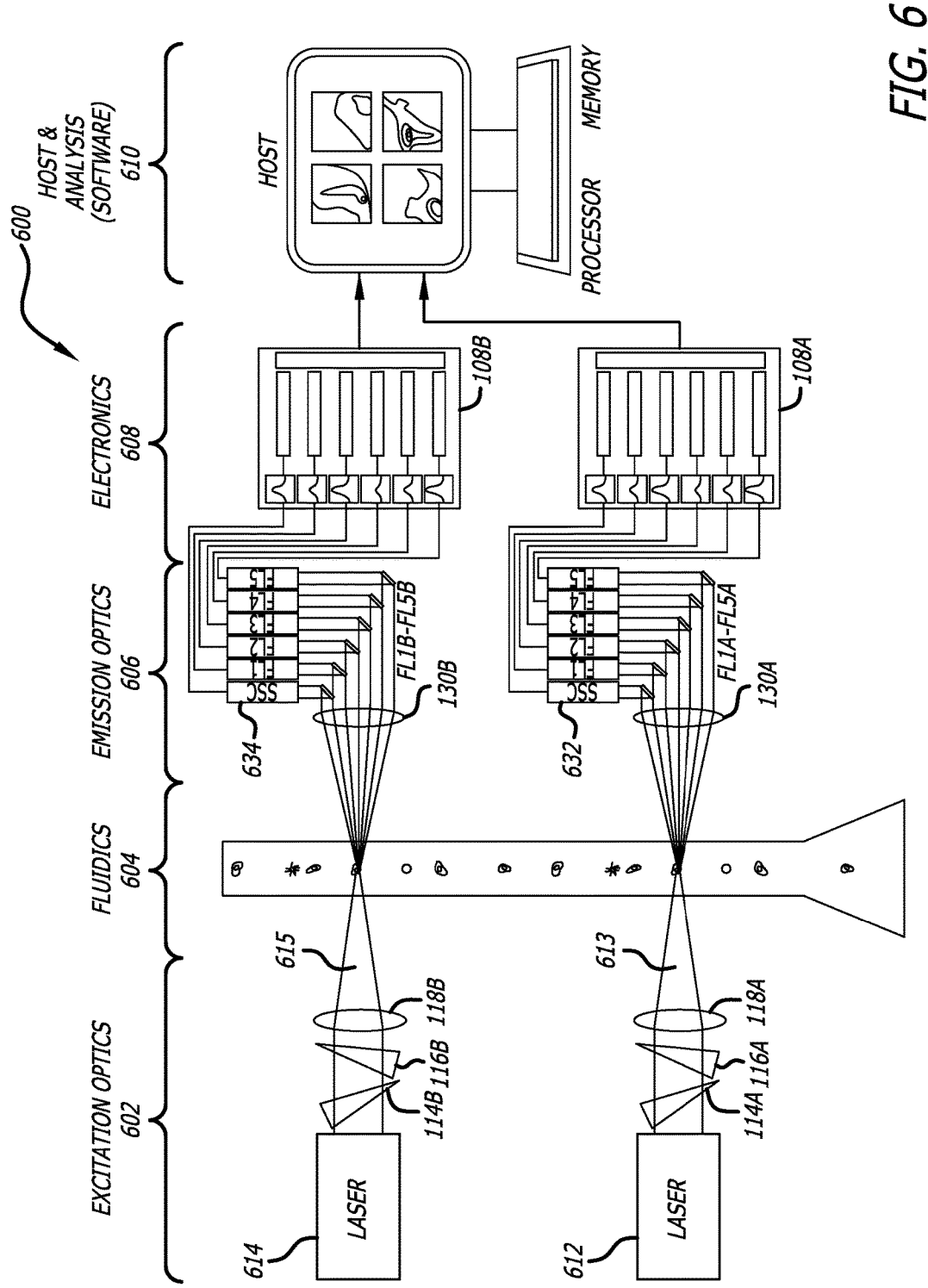
FIG. 6 is a conceptual diagram of a flow cytometry system having dual laser devices and dual scatter channels.

Referring now to FIG. 6, a conceptual diagram of a flow cytometry system 600 is shown. The flow cytometry system 600 has dual laser devices (612, 614) and dual scatter channels (632, 634). Some aspects of the flow cytometry system 600 are similar to the system 100 of FIG. 1. For example, the flow cytometry system 600 has five major subsystems, including an excitation optics system 602, a fluidics system 604, an emission optics system 606, an acquisition system 608, and a host computer with an analysis system 610. The host computer 610 includes a processor with digital mathematical logic and one or more storage devices to store instructions that are executable by the processor to use the digital mathematical logic to generate digital feedback control signals (e.g., average particle flow velocity) that may be used to control one or more features (e.g., one or more valves/pumps/motors in the fluid control system 604 to control sample flow) of the flow cytometry system 600.

However, the flow cytometry system 600 has important improvements over the system 100 of FIG. 1. For example, the flow cytometry system 600 includes an excitation optics 602 with dual lasers devices (612, 614); an emission optics subsystem with dual optics 130A-130B, dual scatter channels (632, 634), and dual fluorescent channels FL1A-FL5A, FL1B-FL1B for acquisition; and an electronics subsystem 608 with dual analyzers 108A-108B for parallel analysis. As further described with reference to other figures, the dual scatter channels (632, 634) perform an important role in calculating the time delay or velocity of a particle within a core stream of a sample fluid so that an average time delay or an average particle velocity can be determined.

A particle often does not fluoresce without a marker. Thus, a fluorescent detector in the fluorescent channels will not detect a particle that does not fluoresce. A scatter channel that detects scattered light can detect a particle from the scattered light whether or not it is marked with a marker. Accordingly, the series of dual lasers 612,614 can excite a particle in a sample flow and the series of dual scatter channels can be used to detect the particle at two points and detect time delay between each or a particle velocity given the known distance between the series of lasers and the time delay.

Figure 7:
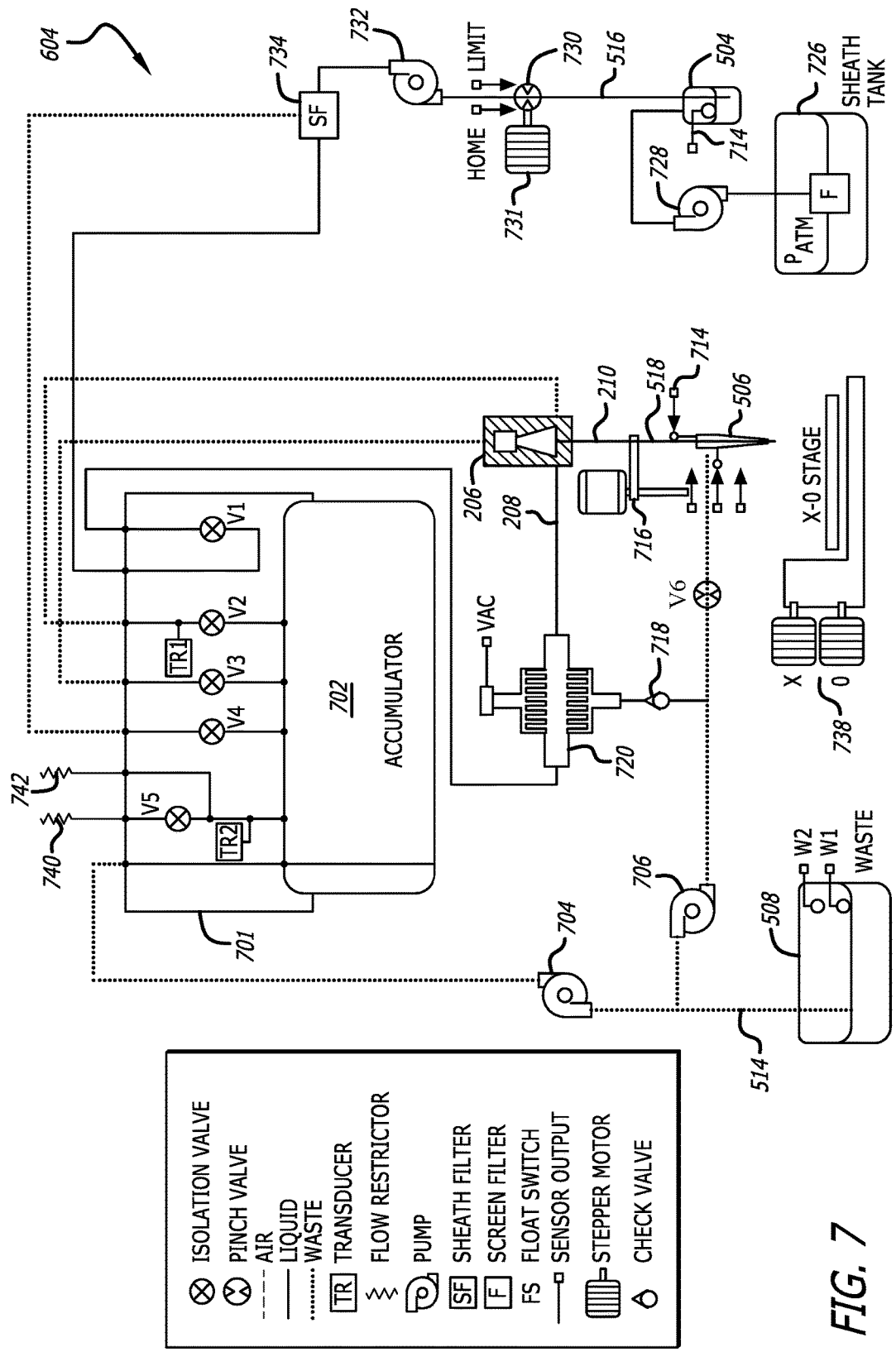
FIG. 7 shows a schematic of the fluidics system of FIG. 6.

FIG. 7 shows a schematic of the fluidics system 604 of FIG. 6. The fluidics system 604 has a vacuum-based fluidics architecture with a pressure regulation scheme based on the time of particle flow between laser beams (613, 615). The fluidics system 604 also provides a continuous sample flow rate adjustment in a vacuum-based system with a sample path completely free of transitions, discontinuities, or potentially cell-damaging peristaltic pumps. The fluidics system 604 seeks to maximize reliability, and instrument up-time by avoiding the use of peristaltic pumps altogether.

The fluidics system 604 includes, without limitation, a manifold assembly 701, isolation valves V1-V5, a pinch valve V6, pressure transducers (e.g., probes) TR1 and TR2, an accumulator vessel (vacuum chamber) 702, a diaphragm vacuum pump 704, a degasser pump 706, sheath fluid 208, sample fluid 210, a sample vessel 506, an output sensor 714, a stepper sit position 716, a check valve 718, a degasser 720, a flow cell 206, a sheath tank 726, a plenum tank 504, a plenum pump 728, a stepper flow control valve 730, a flush pump 732, a sheath filter 734, a waste tank 508, and a plate loader 738, flow restrictors 740 and 742, and a sheath float sensor 744.

The following provides an example run cycle of the fluidics system 604 shown in FIG. 7. On startup, the fluidics system 604 receives feedback from pressure transducers TR1 and TR2. The pressure difference sensed (differential pressure) between transducers TR1 and TR2 is continuous when running and drives the vacuum pump 704 to a minimal value inside accumulator 702 to maintain a constant pressure difference between the inlet 401 and outlet 404 of the flow channel 216 in the flow cell 206 shown in FIG. 4. Pressure transducers TR1 and TR2 may be a differential pressure transducer DPTR to measure the differential pressure between the inlet 401 and the outlet 404 of the flow channel 216 in the flow cell 206. The minimal value is what the fluidics system 604 considers to be a differential pressure (e.g., set-point pressure), at least initially.

It is desirable for the fluidics system 604 to be free of bubbles. Accordingly, the fluidics system 604 has a protocol for opening and closing valves V1-V5 to eliminate gas bubbles. For example, the fluidics system 604 opens valve V4, which pulls gas bubbles out of the sheath filter 734. At any time, if the sheath float sensor 744 in the plenum tank goes below a predetermined low level, then the plenum pump 728 draws fluid from the sheath tank 726. The system is then ready to run.

When the sample vessel 506 is attached, a tube sensor 714 that indicates the fluidics system 604 is ready to lower the sample straw 518 of the system into the sample vessel 506. The platter loader 738 includes a stepper motor that lowers the sample straw 518 into the sample vessel 506. Once the sample straw 518 reaches the stepper sample injection tube position (SITD) 716, one or more sensors cause the fluidics system 604 to open valves V1 and V3. A regulation system in the fluidics system 604 starts driving differential pressure to meet the set-point pressure.

In a favorable embodiment of the fluidics system 604, the vacuum pump 704 evacuates the accumulator vessel 702. The accumulator vessel 702 serves as the driving vacuum source for the system and the diaphragm maintains this source from a differential pressure reference derived from laser delay measurements made by the acquisition system 608. The accumulator vessel 702 also serves as the pulse dampener and constant head reference for the outlet 404 of the flow cell 206, thereby isolating the flow cell 206 from head effects associated with the liquid level in the waste tank 508.

The fluidics system 604 supplies sheath fluid 208 to the flow cell 206 by means of the plenum tank 504. The liquid level in the plenum tank 504 is maintained to a precise level by periodic refilling by means of the plenum pump 728 that draws sheath from the sheath tank 726. In this manner, the plenum tank 504 serves as constant head reference for the inlet of the flow cell 206, thus isolating the flow cell 206 from head effects associated with liquid level in the sheath tank 726.

The manifold assembly 701 includes a network of valves V1-V5, which control fluid flow in the fluidics system 604. In a primary sample acquisition mode, valves V1 and V3 are open. In this mode, sheath fluid 208 and sample fluid 210 are simultaneously drawn into the flow cell 206 by means of a vacuum in the accumulator 702.

When valve V2 is closed, transducer TR1 measures pressure inside the flow cell 206 at the inlet 401, and transducer TR2 measures pressure at the outlet 404 of the flow cell 206 shown in FIG. 4. TR1 pressure measurement via the static line between the flow cell drain port and the closed valve V2 ensures that the differential pressure measurement does not include any dynamic pressure drop associated with the resistance of the sheath inlet port or sheath inlet lines that would otherwise skew the true differential pressure drop of the total flow between the flow channel inlet 401 and flow channel outlet 404. When valves V1 and V3 are open, pressure transducers TR1 and TR2 (or differential pressure transducer DPTR) measure differential pressure across ends of the flow channel 216 of the flow cell 206. The pressure drop between the outlet 404 and the inlet 401, the differential pressure across ends of the flow channel 216, is proportional to the total volumetric flow rate, which is proportional to the core stream velocity (assuming about constant temperature). See Equation 7 for example. Operating temperature is typically between about 15° C. and 20° C., over which viscosity of water can change by as much as 20%. Volumetric flow rate (including sheath fluid velocity) is inversely proportional to viscosity.

As the fluidics system 604 runs, the fluidics system 604 draws sheath fluid 208 and sample fluid 210 simultaneously.

The fluidics system 604 draws sheath fluid 208 from the plenum tank 504 through the stepper flow control valve 730, through the flush pump 732, through the sheath filter 734, through valve V1, through the degasser 720, and to the flow cell 206. Simultaneously, the fluidics system 604 draws sample fluid 210 from the sample vessel 506 to the flow cell 206. By virtue of relative resistances between the sheath straw 516 and the sample straw 518, the fluidics system 604 regulates relative flow rates between the sheath fluid 208 and the sample fluid 210. See Equation 3 for example. The fluidics system 604 (e.g., stepper flow control valve 730 and vacuum pump 704) may regulate the flow rate of the sheath fluid 208 to be, for example, 13 milliliters per minute, while the fluidics system 604 regulates the flow rate of the sample fluid 210 to be, for example, sixteen microliters per minute. Other flow rates are within the scope of the system 600.

The stepper flow control valve 730 controls a continuously variable sample flow rate of fluid flow through the flow cell 206. The sheath straw 516 is inserted into the plenum tank 504. The sample straw 518 is inserted into the sample vessel 506. Compared to the sample straw 518, the sheath straw 516 has a relatively large diameter to handle a relatively large volumetric flow. Conversely, compared to the sheath straw 516, the sample straw 518 has a relatively small diameter to handle a relatively small volumetric flow. The diameter difference between the sheath straw 516 and the sample straw 518 controls the relative volumetric rates in which the sheath fluid 208 and the sample fluid 210 are being sucked from their respective vessels (504 and 506).

With reference to FIGS. 4, 6, and 7, the vacuum pump 704 receives differential pressure feedback from the acquisition system 608 between the pressures sensed by transducers TR1 and TR2 in the fluidics control system 604. Based on the differential pressure feedback, the vacuum pump 704 is controlled to maintain constant core stream velocity even as the stepper flow control valve adjusts to change the sample flow rate. In this manner, the total fluid flow rate through the flow cell 206 can remain substantially unchanged. The sheath flow rate barely changes at all with changes in the stepper flow control valve because the sheath flow rate is so much larger than the sample flow rate. For example, to increase the sample flow rate from 10-ul/min to 30-ul/min, the sheath flow rate would only change from 15.99-ml/min to 15.97-ml/min. The stepper flow control valve enables the system to continuously vary sample flow rate with little to no effect on the sheath flow rate.

With reference to FIG. 7, the stepper flow control valve 730 includes a stepper motor 731 that remotely modulates the flow resistance of the sheath straw 516, which is typically less than that of the sample straw 518. The stepper flow control valve 730 can decrease or increase the flow resistance of the sheath straw 516 while the fluidics system 604 applies about the same vacuum pressure to the fluids. Increasing the flow resistance of the sheath straw 516 causes the fluidics system 604 to increase the amount of sample fluid 210 (relative to the sheath fluid 208) drawn from the sample tank 506. In contrast, decreasing the flow resistance of the sheath straw 516 causes the fluidics system 604 to decrease the amount of sample fluid 210 (relative to the sheath fluid 208) drawn from the sample tank 506. Accordingly, control of the sheath straw 516 by the stepper flow control valve 730 enables the fluidics system 604 to have continuously variable flow rates (e.g., variable sample flow rate and variable sheath flow rate) while maintaining constant total flow, hence a constant (e.g., stable) particle velocity.

Controlling the flow rate of the sheath fluid 208 controls the flow rate of the sample fluid 210, including sample particles in the sample fluid 210. Accordingly, the system 600 can control sheath volumetric flow rate and can thereby control sample volumetric flow rate and particle velocity. The system 600 performs these controls of pressure and velocity in a closed (a.o.t., an open loop). Note that typical commercial systems perform open loop corrections, which requires stopping system pressurization, which is undesirable.

The stepper flow control valve 730 regulates flow rate that passes through, for example, flush pump P2, valve V1, degasser 720, and flow cell 206. Valve V2 gets the flow of fluids running in order to flush the system. Then, valve V2 is closed in order to setup sampling. During cleaning operations before a next sample is sampled, the flush pump P2 pushes sheath fluid through valve V1, degasser 720, and flow cell 206 with valves V2 and V3 closed to enable back flushing of the sample straw 518. Valve V2 is then opened after the back flushing is completed in order to relieve pressure in the flow cell.

Advantageously, the stepper flow control valve 730 and its stepper motor 731 enables fine control of fluids, given the fact that viscosity of the sample fluid 210 can be highly variable. For example, blood as sample fluid 210 can have a viscosity that is double the viscosity of sheath fluid 208. Note that volumetric flow rate is inversely proportional to viscosity.

With valves V1 and V3 open, the fluidics system 604 draws sheath fluid 208 and sample fluid 210 through the top of the flow cell 206, through valve V3, and into the accumulator 702. The accumulator 702 serves as a waste bucket for the fluidics system. Vacuum pump 704 maintains (e.g., regulates) vacuum pressure in the fluidics system 604. Vacuum pump 704 also pumps waste from the accumulator 702 to the waste pump tank 508.

If the sample fluid 210 is running at a high flow rate (e.g., the flow resistance of the sheath straw 516 is substantially high), then the vacuum of the fluidics system 604 is higher in order to maintain differential pressure across the flow cell 206. If the user desires to run a lower flow rate for the sample fluid 210, then the flow resistance of the sheath straw 516 is decreased as appropriate. At this point, the vacuum pump 704 is operating at a relatively high vacuum, which causes the fluidics system 604 to run sheath fluid 208 through the system at much higher velocity, thereby ruining a stable velocity of particles in the sample fluid 210. Accordingly, the fluidics system 604 senses the differential pressure is too high, opens pressure release valve V5, and pulses valve V5 until the differential set-point is met. Accordingly, valve v5 maintains (e.g., regulates) pressure in the system 600.

Restrictors 740 and 742 are always open to the fluidics system 604 to allow partial bleed of fluids into the accumulator 702. So, vacuum pump 704 is always pumping at least a little, which ensures the accumulator 702 remains clean of too much liquid so the accumulator 702 does not fill up.

The degasser 720 removes gas from the fluidics system 604. Generally, any time a vacuum is applied to fluid, gas is generated. Accordingly, degasser 720 removes gas from the fluidics system 604 before the gas reaches the flow cell 206. A degasser pump 706 also serves as a source for sample injection tube (SIT) flush aspiration vacuum.

Every time a sampled fluid 210 (e.g., blood) runs through the fluidics system 604, the sample fluid 210 leaves residue in the SIT line. The residue is highly undesirable because subsequent sample fluid can be contaminated by the residue. Accordingly, the fluidics system 604 achieves SIT flushing with the flush pump 732. If the system is finished running sample fluid, it opens valve V1, but not valve V2 or valve V3. The system then powers flush pump P2 so that the fluidics system 604 pressurizes the entire path of the sheath fluid 208. Because the sheath fluid 208 has no place to go (due to valves V2 and V3 being closed), the fluidics system 604 pushes sheath fluid 208 back through the path of the sample fluid 210, thereby rinsing the inside of the SIT path. The degasser pump 706 sucks up back flush from the SIT path before it can drip onto surfaces below the SIT. This action of the degasser 720 is enabled by valve V6 opening, which causes fluid to flow from the flow cell 206, along the path of valve V6, through the degasser pump 706, and into the waste tank 508. Such flushing cleans both the inside and outside diameters of the SIT (e.g., straw within a straw).

The degasser pump 706 is activated (e.g., turns on) anytime a vacuum switch above the degasser 720 has been triggered due to vacuum going below a predetermined value (e.g., −9 pounds per square inch). The fluidics system 604 pulls gas through the check valve 718. In this case, the amount of gas the degasser 720 pulls from the sheath fluid 208 is relatively low. The degasser 720 remains isolated. While the SIT flush is occurring, the check valve prevents vacuum pressure inside the degasser 720 from being lost.

Anytime the fluidics system 604 lowers gas pressure on fluid, the degasser 720 degasses the fluid. For example, gas forms in the fluid, like gas forming in soda when a pressurized can of the soda is opened. In this system sheath fluid 208 in the plenum tank 504 is at about atmospheric pressure, while pressure in the accumulator 702 is at sub-atmospheric pressure. As sheath fluid 208 travels along the sheath path, pressure on the sheath fluid 208 is continuously decreasing. Because of the continuously lower pressure, bubbles tend to form in the sheath fluid 208. This problem is worse if the sheath fluid was previously aerated. The bubbles tend to be about the same size as particles in the sample fluid 210. Such bubbles cause background optical noise when the fluidics system 604 tries to detect, and analyzes, the particles in the sample fluid 210. Note, for this reason, many manufacturers do not make flow cytometry systems that run with a vacuum. To address the bubbles forming in the sheath fluid 208, the degasser 720 removes the bubbles (e.g., gas) from the fluid solution before the bubbles can enter the flow cell 206.

Figure 8:
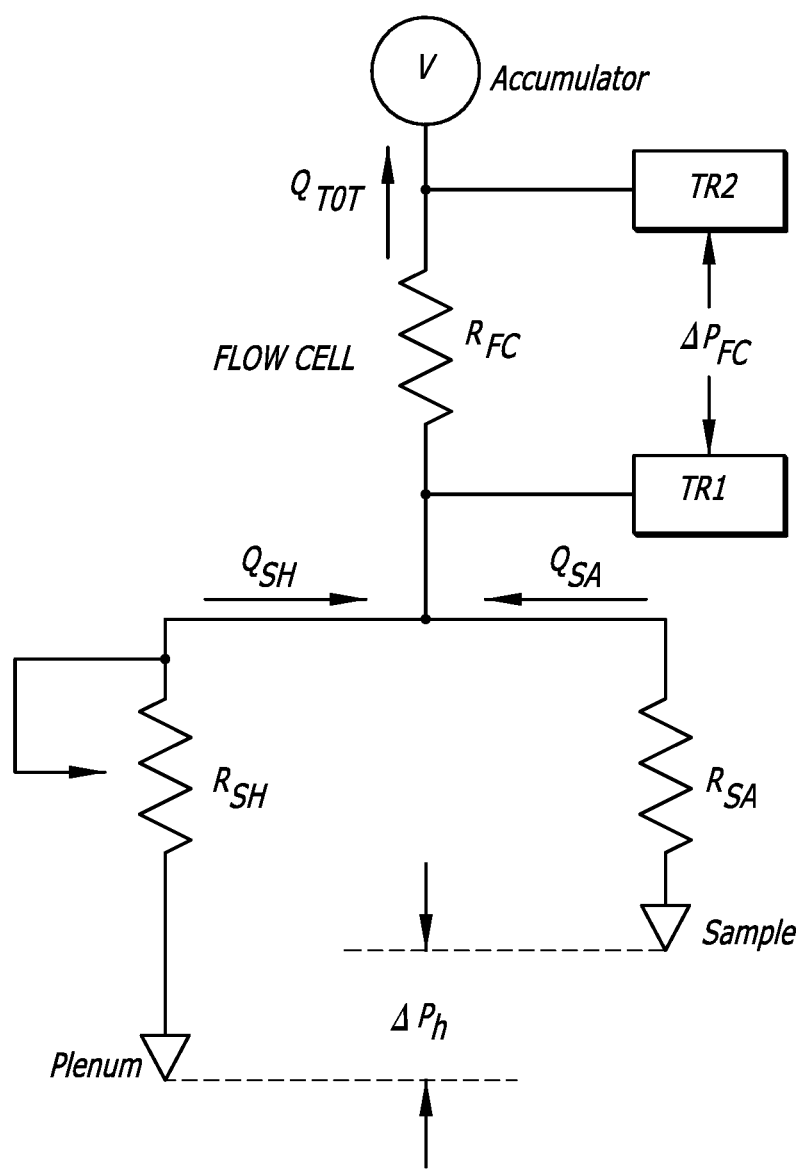
FIG. 8 is a diagram of an electrical circuit that models the primary fluidics flow in the fluidics system.

FIG. 8 is a diagram of an electrical circuit 800 that models the primary fluidics flow in the fluidics system 604. In FIG. 8, the electrical circuit 800 includes, without limitation, a flow cell resistor $R_{FC}$, a variable sheath resistor $R_{SH}$, a sample resistor $R_{SA}$, pressure transducers TR1 and TR2, and accumulator voltage V.

The variable sheath resistor $R_{SH}$ and the sample resistor $R_{SA}$ are coupled in parallel to the flow cell resistor $R_{FC}$. The variable sheath resistor $R_{SH}$ and the sample resistor $R_{SA}$ model the ratio of sheath fluid to sample fluid entering the flow cell 206 at the inlet 401. Using the hydrodynamic equivalent of Ohm's Law and noting conservation of mass, the governing equations for the flow in this circuit 800 are approximated by the following equations:

$$R_{SH} * \dot{Q}_{SH} = R_{SA} * \dot{Q}_{SA} + \Delta P_h \qquad \text{(Equation 3)}$$

where,
$R_{SH}$=sheath channel resistance
$\dot{Q}_{SH}$=sheath fluid flow rate
$R_{SA}$=sample channel resistance
$\dot{Q}_{SA}$=sample fluid flow rate
$\Delta P_h$=hydrostatic pressure difference between sheath plenum level and sample level $$\dot{Q}_{TOT} = \dot{Q}_{SH} + \dot{Q}_{SA} \qquad \text{(Equation 4)}$$

where,
$\dot{Q}_{TOT}$=total volumetric flow rate
$\dot{Q}_{SH}$=sheath fluid flow rate
$\dot{Q}_{SA}$=sample fluid flow rate Equation 3 is analogous to stating, for the vacuum fluidics architecture of the preferred embodiment, the pressure drops across the sheath and sample legs of the primary circuit are equal apart from the hydrostatic head difference between the liquid levels in the sheath plenum and sample vessel. Equation 4 is analogous to stating the total flow rate through the flow cell equals the sum of the sheath and sample flow rates.

While sheath flow rate dominates sample flow rate with respect to the velocity profile for lower sample flow rates, as sample flow rate increases it is technically more accurate to describe things in terms of the total flow rate through the flow cell 206. Substituting Equation (4) into Equation (3) to eliminate sheath flow rate yields the following equation for sample flow rate:

$$\dot{Q}_{SA} = \frac{\dot{Q}_{TOT} - \frac{\Delta P_h}{R_{SH}}}{\frac{R_{SA}}{R_{SH}} + 1} \qquad \text{(Equation 5)}$$

where,
$\dot{Q}_{SA}$=sample fluid flow rate
$\dot{Q}_{TOT}$=total volumetric fluid flow rate
$\Delta P_h$=hydrostatic pressure difference between sheath plenum level and sample level Examination of Equation 5 shows that if the total flow rate is fixed, then the sample flow rate can be easily manipulated by changing the sheath path resistance. In the current invention this is achieved through the use of a stepper motor modulated flow control valve. This allows a continuously variable flow rate of the following range:

$$-\Delta P_h / R_{SA} < \dot{Q}_{SA} < \dot{Q}_{TOT} \qquad \text{(Equation 6)}$$

where,
$\Delta P_h$=hydrostatic pressure difference between sheath plenum level and sample level
$R_{SA}$=sample channel resistance
$\dot{Q}_{SA}$=sample fluid flow rate
$\dot{Q}_{TOT}$=total volumetric flow rate Equation 6 states that if the sheath resistance is infinite, then ideally all of the flow will be through sample path. And if the sheath resistance is zero, then ideally any flow through the sample path will be due to the pressure head between plenum and the sample vessel. However, in practice, the sheath path resistance always has a non-zero value and this value impacts the lower bound of the achievable sample flow rate.

It is also important to realize the impact of the hydrostatic term $\Delta P_h$ on the system performance. If the sample level is below the plenum level, then the sign of the hydrostatic term $\Delta P_h$ is positive. This means that the flow rate range can substantially always span zero for some selection of sheath path resistance $R_{SH}$ and assure sufficiently low flow rates to minimize core stream width. In fact, this can be used to offset the finite value of the sheath path resistance $R_{SH}$ to enable low sample flow rates.

However, if the sample level is above the plenum level, then the sign of the hydrostatic term $\Delta P_h$ is negative. In this case, the sample flow rate will have a positive lower bound that, combined with the non-zero sheath path resistance $R_{SH}$, might be too high to achieve core stream widths as narrow as the particle diameters. This case should be avoided as resolution performance will be limited by the fluidics system due to a higher CV (coefficient of variation, or coefficient of variance).

Figure 9C:
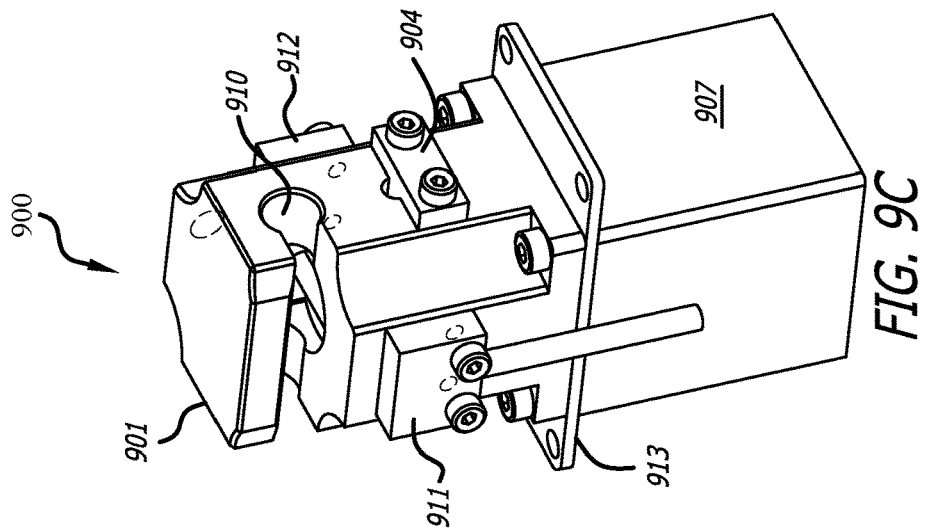
FIG. 9C shows a perspective view of the stepper pinch valve.
Figure 9B:
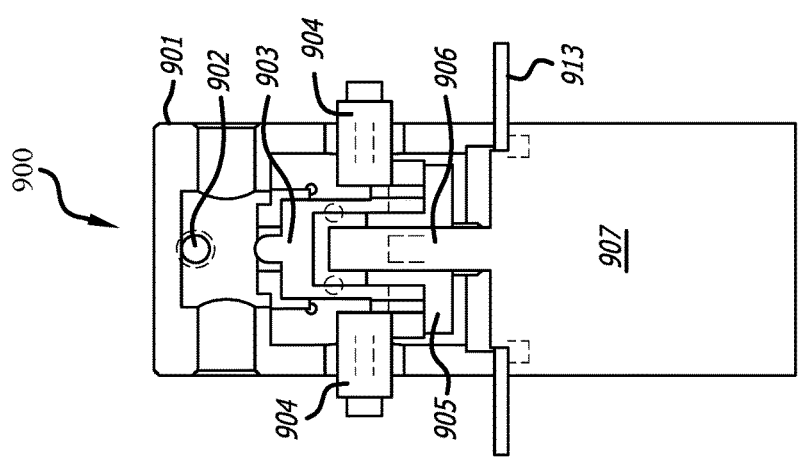
FIG. 9B shows a front, cut-out view of the stepper pinch valve.
Figure 9A:
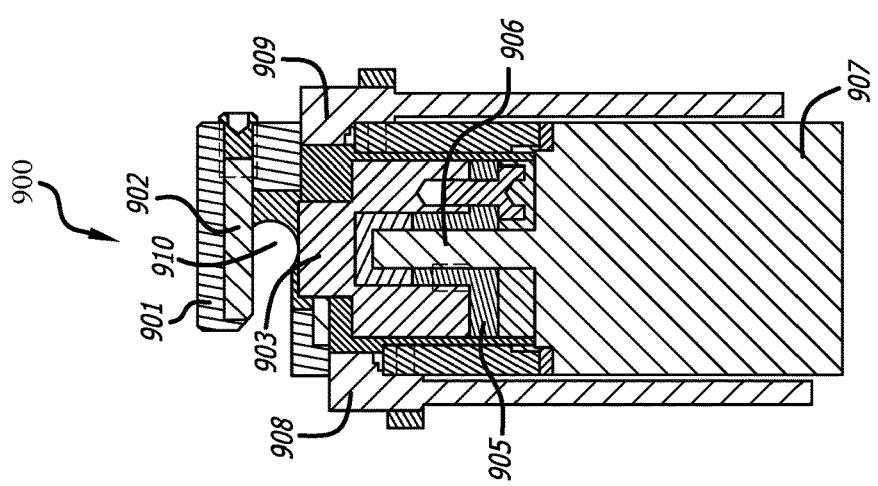
FIG. 9A shows a side, cut-out view of the stepper pinch valve.

FIGS. 9A-9C show various orientations of a stepper pinch valve 900, an embodiment of the stepper flow control valve 730 of FIG. 7. FIG. 9A shows a side cut-out view of the stepper pinch valve 900. FIG. 9B shows a front, cut-out view of the stepper pinch valve 900. FIG. 9C shows a perspective view of the stepper pinch valve 900. The stepper pinch valve 900 includes, without limitation, a head 901, a pinch anvil 902, a pinch hammer 903, hammer guides 904, a nut 905, a lead screw 906, a stepper motor 907, sensors 908 and 909, a tubing passage 910, a home switch 911, a limit switch 912, and a mount plate 913. The stepper flow control valve 730 may also be referred to as a stepper motor modulated flow control valve because it includes a stepper motor that modulates a valve and the rate of flow. Accordingly, the stepper pinch valve 900 may also be referred to as a stepper motor modulated pinch valve 900 because it includes a stepper motor 907 that modulates a valve and the rate of flow.

The stepper motor 907 rotationally drives, and is couple to, the lead screw 906. The nut 905 is threaded on, and is couple to, the lead screw 906. The nut 905 is in mechanical communication with the pinch hammer 903, which is in mechanical communication with the pinch anvil 903. The rotational motion of the lead screw 906 generates translation motion of the nut 905. The translational motion of the nut 905 generates translational motion of the pinch hammer 903 to/from the pinch anvil 902. The translational motion of the pinch hammer 903 changes (e.g., decreases/increases) the spacing (e.g., diameter) of the tubing passing 910. The tubing passing 910 is a concave cavity formed between the pinch hammer 903 and the pinch anvil 902. The sheath straw 516 passes through the tubing passing 910 and may make contact with the pinch hammer 903 and the pinch anvil 902. Accordingly, the diameter of the sheath straw 516 changes (e.g., decreases or increases) according to the spacing of the tubing passing 910. The hammer guides 904 keep the pinch hammer 903 from spinning with the motor shaft. Accordingly, the pinch hammer 903 receives a vertical movement via a translation of rotation of the lead screw 906.

The sensors 908 and 909 are in mechanical communication with the pinch hammer 903 and or the pinch anvil 902. The sensors 908 and 909 detect when the pinch hammer 903 or pinch anvil 902 is at a limit. At startup of the system 600, the system 600 determines, via the sensors 908 and 909, a position of the pinch hammer 903 within a range of motion of the pinch hammer 903. For example, an algorithm in firmware of the system 600 auto-cycles the pinch hammer 903 in translational motion to trigger sensors 908 and 909. The system 600 calibrates the position of the pinch hammer 903. Once the system calibrates the position of the pinch hammer 903, the system 600 is configured for setting the values of the pinch hammer 903 (e.g., diameter of tubing passage 910) between translation motion limits, in order to achieve particular flow rates.

The following is an example of open loop calibration of the pinch hammer 903. The system 600 finds the position of the stepper motor 907 (and thus pinch hammer 903) when the flow rate of the sheath fluid 208 is zero. In open loop mode, a titration is performed on a stepper value to get a specific flow rate. For instance, assume a stepper motor range of 1 to 1,000 steps. The system 600 may determine that step #540 corresponds to a flow rate of 60 millimeters per minute, while step #800 corresponds to a flow rate of 120 millimeters per minute. These stepper values and corresponding flow rates are saved for the system to interpolate other subsequent settings of the stepper motor for a desired flow rate. In this example, the flow rate is linearly proportional to the stepper number. This open loop calibration technique is fairly robust and accurate.

An alternative to using an open loop calibration is using a feedback device (e.g., a thermal pulse flow meter) that measures volumetric flow rate. For example, the system 600 may receive input that requests a sample fluid flow rate of 60 microliters per minute. A feedback circuit that is coupled to the feedback device drives the stepper motor 907 into position until the flow rate reaches about a predetermined rate, such as 60 microliters per minute. Such flow rate calibration may be referred to as closed loop feedback with a thermal pulse flow meter.

Referring back to FIG. 7, a stepper motor modulated flow control valve 730 represents a significant improvement over discrete resistance flow paths or coiled tubing compression mechanisms (e.g., such as found in U.S. Pat. No. 8,528,427 titled DUAL FEEDBACK VACUUM FLUIDICS FOR A FLOW-TYPE PARTICLE ANALYZER filed by Vrane and Norton), while maintaining an obstruction free sample path. Further, this simpler fluidics system 604 lends itself to continuous feedback control of the sample flow rate.

In another embodiment, a non-invasive flow meter (e.g., a SENSIRION SLI flow meter) in the sample path provides feedback to the stepper position of the modulated flow control valve. This allows the system to provide true sample flow rate control without involving the complexity, expense, or reliability problems associated with syringe drives. The stepper pinch valve 900 is one embodiment of a stepper flow control valve 730 that can be used in the system. Other types and embodiments of flow control valves can be used in the system to control the flow of fluids.

FIGS. 10A-10B show more details of the fluidics system 604, the emission optics 606, and the acquisition system 608 shown in FIG. 6. Direct control of the core stream velocity is achieved by utilizing a dual laser delay measurement made by the acquisition system 608 based on particle flow in the fluidics system 604. The time delay measurement ΔT between a particle passing dual lasers can be used as a proxy for particle velocity and generate a feedback control signal of average time delay to control flow rate in the flow channel. Alternatively, with the known distance L between lasers, particle velocity can be computed and used to generate average particle velocity as a feedback control signal to control flow rate in the flow channel. To maintain the average particle velocity at a desired constant, the vacuum pump may be controlled to control core flow velocity and maintain the average time delay or average particle velocity constant.

In order to utilize the widest bandwidth of emitted light to identify biological particles (e.g., cell-lines), the fluidics system 604 uses dual laser devices (laser 612, laser 614) that emit two laser beams (laser beam 613, laser beam 615) typically having two excitation laser wavelengths. Dual serial scatter channels (scatter channel 632 and scatter channel 634) are used to detect scattered light from the two laser beams (laser beam 613, laser beam 615) of known separation at different points in time in the flow channel.

The system 600 takes advantage of the concept that a particle passing through a laser beam (613 or 615) always produces scattered light but does not always fluoresce. The system 600 detects the scattered light off a particle with dual scatter channels (scatter channel 632, scatter channel 634) in order to calculate the velocity of particles within the sample fluid. The laser beams (613, 615) are spatially separated by a known predetermined distance L shown in FIG. 10A. The laser separation distance L shown in FIG. 10A may be minimized as much as possible up to a limit of cross talk between the dual lasers 612,614 generating the laser beams 613,615.

A particle 1006 first flows (e.g., passes) through the first laser beam 613 and causes the emission optics 606 to generate a pulse 1012 measuring scattered light off the particle by the first laser beam. The particle 1006 continues its flow in the flow channel and secondarily flows (e.g., passes) through the second laser beam 615. The emission optics 606 generate a pulse 1014 measuring scattered light off the particle by the second laser beam.

The scatter channel 632 senses the pulse 1012 with an optical detector (e.g., photo detector) and sends pulse information to the acquisition system 608. The pulse information from the first scatter channel 632 may include, for example, a particle identifier (e.g., particle 1006), a laser identifier (e.g., laser device 612 or laser beam 613), and a first timestamp (e.g., timestamp #1), among other information. The second scatter channel 634 senses the second pulse 1014 with a with an optical detector (e.g., photo detector) and sends pulse information for the second pulse to the acquisition system 608. The pulse information from the scatter channel 634 may include, for example, a particle identifier (e.g., particle 1006), a laser identifier (e.g., laser device 614 or laser beam 615), and a timestamp (e.g., timestamp #2), among other information.

Figure 10C:
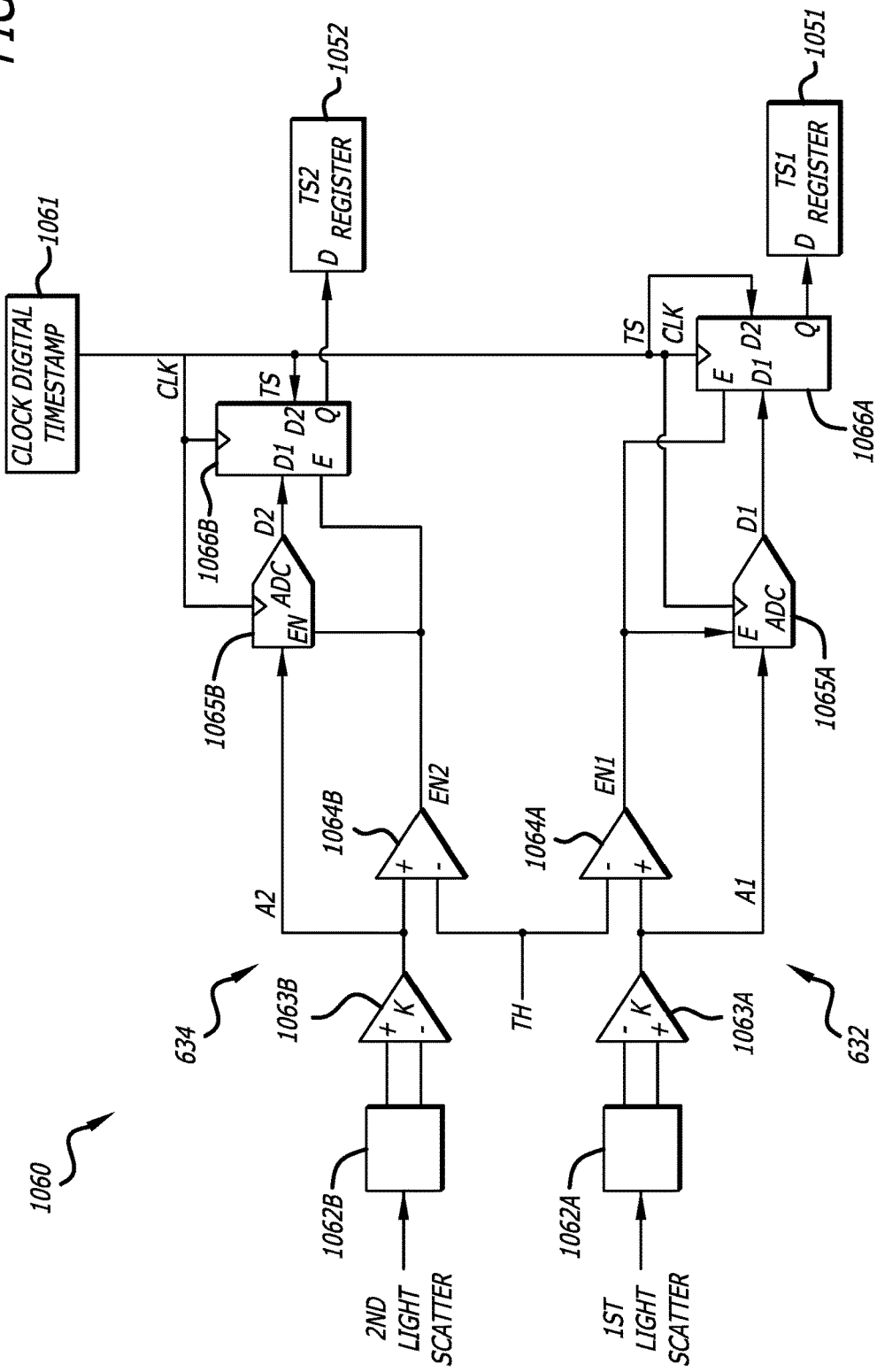
FIG. 10C is a block diagram of a peak sampling circuit to determine the time stamps at the peaks of the scattered light in the dual scatter channels.

Referring now to FIG. 10C, a block diagram of a peak sampling circuit 1060 is shown to determine the time stamps from the two peaks of the pulse signals 1012,1014 representing the scattered light sensed by the first scatter channel 632 and the second scatter channel 634. The first scatter channel 632 includes an optical detector 1062A with outputs coupled to a low noise gain amplifier 1063A to generate the pulse signal 1012 shown in FIG. 10B. The second scatter channel 634 includes an optical detector 1062B with outputs coupled to the inputs into a low noise gain amplifier 1063B to generate the pulse signal 1014 shown in FIG. 10B.

The circuit 1060 further includes a clock or timer 1061 that generates a clock signal CLK and a time stamp signal TS. The clock signal CLK is used to synchronize circuits and devices together. The time stamp signal TS is used to time stamp the digital samples of the scatter pulses 1012,1014 and obtain the time difference between a particle passing the first scatter channel 632 and the second scatter channel 634.

Figure 10D:
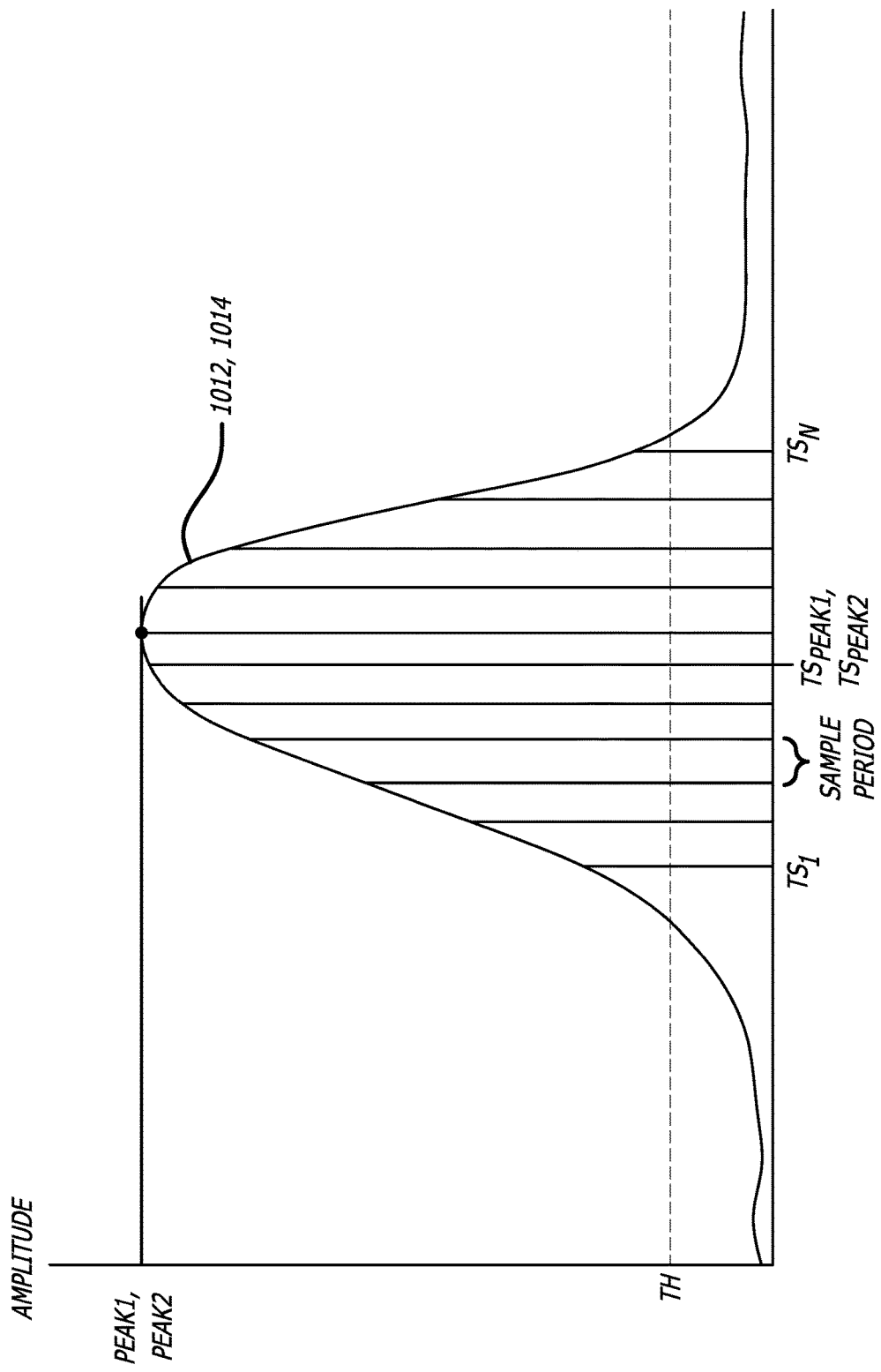
FIG. 10D is a waveform diagram illustrating digital sampling of a scattered light waveform in order to determine the peak amplitude and the time stamp associated with the peak amplitude.

FIG. 10D illustrates the pulse signal 1012,1014. It is desirable to periodically sample the pulse signals 1012,1014 to generate a plurality of digital signals with respective time stamps. A threshold value TH is set upon which to enable digital sampling of a pulse. Amplitude values in the pulse signal below the threshold are considered to be noise disabling or terminating the digital sampling of the pulse. Once the threshold is exceeded by the pulse amplitude, digital sampling begins with a first sample being captured at time stamp TS1. N samples may be captured at time stamps separated by the sample period. The last sample is captured at a time stamp TSN after which the amplitude of the pulse signals drops off below the threshold value TH thereby indicating a completion of a digital capture of the pulse.

Referring back to FIG. 10C, the threshold value TH is coupled into one input of comparators 1064A-1064B for each scatter channel. The analog output A1,A2 of the gain amplifier 1063A-1063B is coupled into the second input of the comparators 1064A-1064B. The comparators 1064A-1064B compare the amplitude of the pulse signals with the threshold values. If the comparators determine the amplitude of the pulse signals are above the threshold value TH, they generate enable signals EN1,EN2 at their output terminals to start digital sampling. When the comparators sense the amplitude of the pulse signals go below the threshold TH, they shut off the enable signals EN1,EN2 to stop any further digital sampling of the pulses because the amplitude may be considered in the noise.

The analog output A1,A2 of the gain amplifier 1063A-1063B is also coupled into the analog input terminal of analog to digital converters (ADC) 1065A-1065B. The clock signal is coupled into the clock terminals of the analog to digital converters (ADC) 1065A-1065B. The enable outputs EN1,EN2 from the comparators 1064A-1064B are coupled into the enable input terminals of the analog to digital converters (ADC) 1065A-1065B. The digital output D1,D2 of the analog to digital converters (ADC) 1065A-1065B is coupled into the first data input of the dual port storage devices 1066A-1066B to store the digital data sample. The time stamp TS output from the clock circuit 1061 is coupled into the second data input of the dual port storage devices 1066A-1066B to store the time stamp associated with each digital data sample.

The clock signal is coupled into the clock terminals of the analog to digital converters (ADC) 1065A-1065B and the clock terminals of the dual port storage devices 1066A-1066B to concurrently store together the digital sample and the time stamp. The enable outputs EN1,EN2 from the comparators 1064A-1064B are further coupled into the enable terminals of the dual port storage devices 1066A-1066B to enable storage of the plurality of digital samples D1,D2 into the dual port storage devices 1066A-1066B representing the pulses 1012,1014.

The dual port storage devices 1066A-1066B are coupled to the TS1 and TS2 registers/flip flops 1051-1052 to transfer the respective output TSpeak1, TSpeak2. The output of the dual port storage devices 1066A-1066B are coupled to the data input of the TS1 and TS2 registers/flip flops.

The dual port storage devices 1066A-1066B store each digital sample associated with each time stamp. It is desirable to search for the peak amplitudes Peak1,Peak2 in each pulse signal and select the associated time stamp as the peak time stamps TSpeak1,TSpeak2. As seen in FIG. 10D, the largest digital sample value represents the peak amplitude Peak1,Peak2 of the pulse 1012,1014. The time stamps associated with the peak amplitude Peak1,Peak2 are the peak time stamps TSpeak1,TSpeak2 at the respective peak Peak1,Peak2 of the pulse 1012,1014.

To determine the peak amplitude Peak1,Peak2 and select the respective time stamps TSpeak1,TSpeak2, the dual port storage devices 1066A-1066B may be sortable tables. In this case they that are sorted so that sample values for the peak amplitude Peak1,Peak2 can be determined having the largest digital values and their associated time stamps selected as the peak time stamps TSpeak1,TSpeak2. In another case, the dual port storage devices 1066A-1066B may include a logical comparison capability to point out the peak amplitudes Peak1,Peak2 and the associated peak time stamp TSpeak1,TSpeak2 for each pulse 1012,1014.

The peak time stamp TSpeak (e.g., TSpeak1 and/or TSpeak2) for the peak amplitude in each pulse for a particle is stored in the registers 1051,1052. With the peak time stamp TSpeak for each pulse stored in a register, a subsequent digital subtraction may be made to determine the time difference as further explained below.

Referring back to FIG. 10B, the acquisition system 608 may further include, a data acquisition chip DAC 1002 that includes particle calculation logic 1050 in a field programmable gate array (FPGA), among other devices. The particle calculation logic 1050 is coupled to the scatter channels 632,634 to receive pulse information and generate a digital time stamp. The logic 1050 includes a time keeping device such as the clock or timer 1061 to generate the digital time stamp in response to the sampling of the pulse information by the ADCs 1065A-1065B. The particle calculation logic 1050 includes the registers/flip-flops 1051,1052 storing the digital values for the first peak time stamp TSpeak1 and the second peak time stamp TSpeak2. A digital mathematical logic device (adder or subtractor) 1053 is coupled to the registers 1051,1052 to receive the digital time stamps and compute the time difference between the first peak time stamp TSpeak1 and the second peak time stamp TSpeak2.

A packetizer 1004 is coupled to the particle velocity calculation logic 1050 and the scatter channels 632,634. The packetizer 1004 collects and assembles the information together into an event data packet regarding the particle 1006 flowing in the flow channel past the two laser beams 613,615. An event data packet is generated for each particle in the flow and sent to a host computer executing acquisition software instructions as a part of the acquisition system. The event data packet includes the pulse information for each scatter channel as well as the time difference between peak time stamps.

For each particle of a plurality of particles in a flow, the acquisition system 608 has at least the following information: the distance L between the laser devices (612, 614), the particle identifier, the laser identifiers, the corresponding timestamps, and the time difference between peak time stamps (time delay) for each particle. The time delay for each particle can be stored in a storage device and accumulated so that the average time delay can be determined. The average time delay may be determined by summing together an accumulation of time delays and dividing by the total number of particles associated with those time delays. The average time delay can be used to generate a control signal to maintain a constant flow rate or velocity of particles and a constant average time delay.

The acquisition system 608 with a digital mathematical logical device (e.g., device 1053 or a host computer 610 with processor logic, memory, and instructions) may further calculate the particle velocity of each particle according to Equation 8 (e.g., particle velocity equals the distance L divided by the time difference between time stamps) and include it as part of the event data packet regarding a particle. With multiple particles flowing in the flow channel over a known time period, the system (e.g., device 1053 or a host computer 610 with processor math logic, memory, and instructions) can accurately calculate an average particle velocity for multiple particles passing over a period of time.

The particle velocity for each particle can be stored in a storage device and accumulated so that the average particle velocity can be determined. The average particle velocity may be determined by summing together an accumulation of particle velocities and dividing by the total number of particles associated with those particle velocities.

Regarding identifying each particle, the density of particles in the sample fluid is relatively low such that particles do not pass by the laser devices (612, 614) excessively often. For example, the fluidics system 604 may operate with a sample flow rate and a particle density such that particles flow through the laser devices (612, 614) at less than 10,000 particles per second (e.g., events per second) and an average particle velocity of about 5 meters per second. In this example, 10,000 particles per second (e.g., events per second) may be referred to as the "event rate" or particle frequency. With such an event rate and average particle velocity, the separation between particles is typically going to be between about 150 micrometers and 200 micrometers, which is plenty of separation to have a sufficiently high signal-to-noise ratio.

In contrast, if the particles were to pass by the laser devices (612, 614) at a higher even rate of 50,000 particles per second with the same flow rate, for example, then the fluidics system 604 may generate an overly high amount of particle coincidence between the laser devices (612, 614). In such case, the system 600 may erroneously interpret two different particles as being the same particle due to the reduced particle separation required for the higher event rate. Such coincidence may cause an unduly low signal-to-noise ratio and may render the calculations of the acquisition system 608 to be unreliable.

Fortunately, it is easy for the system 600 to keep separation between particles sufficiently large such that coincidence is not an issue. Further, the system 600 calculates the average particle velocity of multiple particles over a period of time. The average particle velocity can be used as a feedback control signal to adjust flow rate as needed maintain a high signal to noise ratio in each of the two scatter channels. So, any coincidence that may occur can be treated as an outlier, as long as separation between particles is kept sufficiently high.

Typical commercial flow cytometer systems are fundamentally different. A typical commercial system may have dual lasers, but the dual lasers are not being used to measure velocity of particles. A typical commercial system may have only one side scatter channel to detect scattered light off a particle by a first laser at one position. The second laser usually has only fluorescence detectors that only sense fluorescence from a marker coupled to the particle. Particles are not always marked with a fluorescent marker and even if marked, they may not always fluoresce due the wrong wavelength of excitation laser light. With the second laser associated with a fluorescent detector and not a scatter channel, only fluorescence from a marker attached to the particle can be detected. A typical commercial system cannot calculate particle velocity by using fluorescence only because particles may not be labeled with fluorescent markers that fluoresce under both lasers exciting at different wavelengths. For example, consider a particle in a sample that is chemically dyed red with a fluorescent marker that fluoresces when excited by a laser of red wavelength but not a laser of blue wavelength. Typically, the dual lasers have different wavelengths one laser to excite and detect particles that are dyed red and another laser to excite and detect particles that are dyed blue, but not a laser that excites both. Accordingly, with only one of two lasers exciting each fluoresced particle in a sample flow, particle velocity cannot be measured with two fluorescent detectors. Two scatter channels can detect a particle when it flows by the associated lasers, regardless of the fluorescent dye marker and regardless of laser excitation wavelength.

In contrast to typical commercial systems, the system 600 takes advantage of the fact that a particle passing through a laser beam (613 and 615) consistently produces scattered light. Accordingly, the system 600 is configured with the dual scatter detector channels (632, 634) to twice detect the scattered light off a particle from being struck by both laser beam 613 and laser beam 615.

The core stream velocity is proportional to the volumetric flow rate in the flow channel 216. In a technically accurate sense, the core stream velocity is proportional to the total flow rate in the channel. Further, the total volumetric flow rate is proportional to the differential pressure across the ends of the flow channel. For sake of completeness, these relationships can be formally expressed as the following equation:

$$V \propto \dot{Q}_{TOT} \propto \Delta P_{FC} \quad \text{(Equation 7)}$$

where,
V=core stream velocity
$\dot{Q}_{TOT}$=total volumetric flow rate
$\Delta P_{FC}$=differential pressure across flow channel Laser delay describes particle flow time between two spatially separated laser beams (613, 615), as shown in FIG. 10A. Referring to FIGS. 10A-10B, laser delay can be determined from the difference between time stamps associated with signal pulses detected by the in line detector channels (632, 634) for the same particle 1006. In one embodiment, the laser beams (613, 615) can render a laser delay that is precise to within about ±0.1 microseconds. Laser delay is related to the particle velocity by the following equation:

$$\Delta T = L/V \quad \text{(Equation 8)}$$

where,
$\Delta T$=flow time of a particle between spatially separated laser beams
L=distance between the spatially separated laser beams
V=core stream velocity Laser delay is an important parameter of data acquisition in flow cytometers with spatially separated laser beams (613, 615). The precise knowledge of its value allows the acquisition system to associate pulses from different laser beams (613, 615) with the same particle 1006. Referring again to FIG. 10B, pulse 1012 is generated when the particle passes through laser beam 613. Shortly thereafter, the particle will generate pulse 1014 when the particle passes through laser beam 615. If the acquisition system 608 knows the correct laser delay, then the acquisition system 608 can correctly associate pulse 1012 and pulse 1014 with the same particle. Calculation of the laser delay is usually performed as part of daily quality control procedures for the cytometer and assumed to remain constant for the rest of the day. In this example the acquisition system 608 includes electronics, such as a DAC (digital-to-analog converter) 1002 integrated in an FPGA (field programmable gate array).

In practice, however, there exists a certain degree of uncertainty in the laser delay, mostly due to variations in core stream velocity. These variations can arise from many sources, such as the following: changes in liquid levels, temperature shifts, particle position in the core stream, drifts in laser position, and so on. To make up for the uncertainty in the laser delay, acquisition systems employ the concept of window extension. Window extension adds a tolerance zone to the pulse width measured at laser beam 613 and applies this increased window as the expectation interval to collect pulse 1012. The increased window is essentially a fluidics system forgiveness factor that allows the acquisition system 608 to associate pulses over a range of laser delays. Larger window extensions allow for greater velocity variations, but at the expense of a lower signal-to-noise ratio because more background light is integrated into pulse 1014 (second pulse) over the part of the collection interval where there is no particle signal.

A favorable embodiment of the system 600 employs continuous monitoring of the laser delay by the acquisition system 608. A running average of the laser delay value is fed to the fluidics system 604 and is used to periodically correct the differential pressure set-point value to insure the laser delay remains within very tight tolerances. Such feedback (e.g., correction) ensures the window extensions approach being the smallest possible. A basic algorithm for the differential set-point correction is given by the following equation:

$$\Delta P_{SP,new} = \frac{L}{K_3 * \Delta T_{old}^2} \{\Delta T_{new} - \Delta T_{old}\} + \Delta P_{SP,old} \quad \text{(Equation 9)}$$

where,
$\Delta P_{SP}$=the differential set-point pressure for the pressure regulation feedback loop
$\Delta T$=laser delay
L=distance (e.g., spacing) between dual laser beams
$K_3$ is an empirical constant associated with the resistance of the of the flow cell with a range given by the following equation:

$$1\sqrt{2\rho \Delta P_{SP,old}} < K_3 < \frac{D_h^2}{16\mu Z} \quad \text{(Equation 10)}$$

where,
ρ=sheath fluid density
μ=sheath fluid viscosity
$D_h$=hydraulic diameter of the flow channel
Z=length of the flow channel Equation 10 represents the possible range of flow regimes inside the flow channel. The lower limit represents flow resistance due to purely inviscid (Bernoulli) flow. The upper limit represents flow resistance due to purely viscous (Poiseuille) flow.

Referring again to FIGS. 7 and 8, the laser delay corrected differential pressure set-point is used in a feedback loop where the feedback parameter is the differential pressure measured across the ends of the flow cell 206. The system gain, G, includes a PID (proportional-integral-derivative) controller and the physical characteristics of the vacuum pump 704, the accumulator 702, and primary flow path resistance network ($R_{FC}$, $R_{SH}$, $R_{SA}$) and pressure transducers (TR1, TR2).

Typical flow cytometers may use differential feedback. However, typical flow cytometers are hampered by a clumsy sample flow rate scheme that requires switching between differential and static feedback modes between running and stopped states. They also require a temperature input to compensate for viscosity changes.

Advantageously, the embodiments of the invention have no need for either of those commercially available schemes. Utilizing laser delay provides a direct measurement and control of core stream velocity. Temperature compensation is unnecessary because thermal effects represent a contribution to laser delay shift. Given stable laser spacing, using laser delay as a feedback parameter essentially reduces to using core stream velocity as a feedback parameter to maintain itself. A fairly important nuance is that, as a correction to the differential set-point, the laser delay serves as an outer loop of a compound feedback system. The differential pressure serves as an inner loop. This allows the acquisition system 808 to calculate an accurate running average based on thousands of laser delay measurements. In the absence of events (e.g., particles) the system maintains pressure differential based on the last updated set-point correction. This prevents the system from going "open loop" and insures robust control.

In typical fluidics systems, the described clumsiness of the sample flow rate management arises from limitations in the vacuum feedback scheme. Such a system does not incorporate any pressure feedback mechanism that can relieve vacuum in the accumulator. Their vacuum pump can only increase, or maintain, vacuum level in the accumulator. This vacuum pump limitation is particularly cumbersome because in order to reduce sample flow rate, while maintaining constant total flow rate, the system must reduce accumulator pressure in response to the lower sheath path resistance. Such a system only achieves this reduction by flooding the accumulator (compromising waste head level) with sheath fluid directly from the plenum as a special run case. During this special run case, which takes considerable work flow time, the acquisition system must be disabled.

Advantageously, the system 600 completely solves this problem of typical systems by incorporating a dedicated vacuum air bleed valve (e.g., valve V5 in FIG. 7) controlled by a pressure relief algorithm that is part of the vacuum feedback control loop.

Feedback Control Methods and Systems for Vacuum

Figure 11:
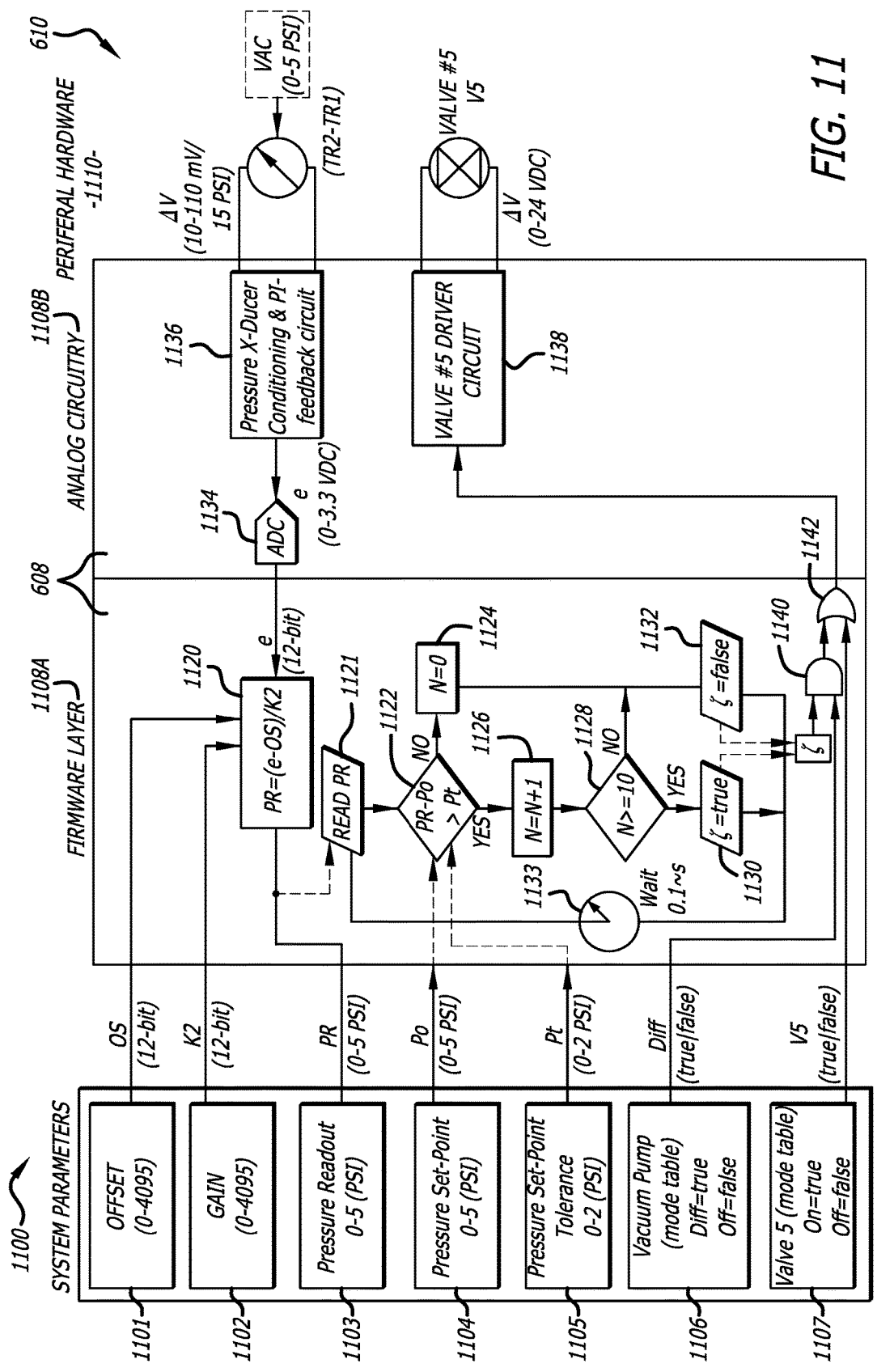
FIG. 11 is a flowchart for an example method to control vacuum relief in the fluidics system.

FIG. 11 is a block diagram of a feedback control system and method 1100 to control vacuum relief in the fluidics system 604 of a flow cytometry system. A vacuum pump cannot operate in reverse. Accordingly a vacuum relief valve, such as valve V5 in FIG. 7, may be used to supply air more quickly to the accumulator 702 to solve an over vacuum condition.

In one embodiment, the acquisition system 608 carries out the method 1100 to control the valve V5 coupled between the accumulator 702 and a flow restrictor 740 to atmospheric pressure shown in FIG. 7. The acquisition system 608 may include, for example, a firmware layer 1108A to execute control processes and analog interface circuitry 1108B to interface with peripheral hardware 1110. The analysis system 610 may include, for example, peripheral hardware 1110 that it interfaces with to sense and control vacuum in a flow cytometry system. The peripheral hardware 1110 includes pressure transducers TR2-TR1 (or the differential pressure transducer DPTR) to sense the differential pressure across ends of the flow channel 216 of the flow cell 206 and control the controllable valve V5 to release vacuum in the accumulator 702 to the atmosphere thereby increasing pressure therein to alter the differential pressure.

Using the system and method 1100, the valve V5 operates as a pressure (vacuum) releasing mechanism to correct pressure (e.g., pounds per square inch or PSI) in the accumulator 702 shown in FIG. 7. The system and method 1100 enables the fluidic system in the flow cytometry system to be continuous and far more responsive than typical flow cytometry systems. The method 1100 also eliminates the need for so-called dual feedback loops (static and dynamic) used in other flow cytometry systems (such as described in U.S. Pat. No. 8,528,427 titled DUAL FEEDBACK VACUUM FLUIDICS FOR A FLOW-TYPE PARTICLE ANALYZER issued to David Vrane et al. on Sep. 10, 2013).

The system parameters for the feedback control system and method 1100 include, without limitation, the input system parameter of an offset 1101, a gain 1102, a pressure set-point 1104, a pressure set-point tolerance 1105, a vacuum pump state 1106, and a valve 5 state 1107 and an output system parameter of a pressure readout 1103.

Valve 5 is opened to more rapidly release vacuum in the accumulator 702 of the fluidic system than is being bled out to the atmosphere by the flow restrictor 742. Generally, during normal operation of the vacuum pump 704, valve V5 is periodically opened for a short period of time. There are out of ordinary cases where valve V5 is periodically opened.

If there is a need for complete vacuum release, such as during system cleaning cycles, the valve 5 state 1107 is set to true to bypass much of the firmware logic through the OR gate 1142, and open valve V5 for a period of time until the valve 5 state 1107 is set to false.

If the vacuum pump 704 is not being used, little vacuum may be present in the accumulator and there is no need to control valve V5 to be open and dump vacuum in the accumulator 702. In this case, the vacuum pump state 1106 may be set false indicating an off condition. The vacuum pump state is one of two inputs to the AND gate 1140. In the case the vacuum pump state is set to false, the processes in generating the bit value ζ are ignored and the output of the AND gate 1140 is false. In this case, but for the valve state V5 1107, valve V5 is not controlled to be open and dump vacuum in the accumulator 702.

The firmware layer 1108A includes a number of actions or processes and logic that interface with the system parameters.

At action 1120, the system receives the pressure readout 1101, the gain 1102, and a digital feedback error signal e from the analog circuitry 1108B. The system calculates the pressure readout 1103 using the gain factor K2 1102 and the offset OS 1101 based on the error signal e.

At action 1121, the system reads the pressure readout 1103 and/or a delay parameter 1133 before performing a comparison at action 1122.

At action 1122, the system determines if the pressure readout 1103 minus the pressure set-point 1104 is greater than the pressure set-point tolerance 1105. If not (no), the system goes to action 1124, where the system sets a counter N to zero (0) and jumps to action 1132. However, if so (yes) the system goes to action 1126, then the system increments the present counter value N and goes to action 1128.

At action 1128, the system determines if the counter value N is greater than or equal to a predetermined number (e.g., ten). If yes at action 1128, then the system sets a bit value ζ equal to true (logical 1). However, if no at action 1128 or action 1122, then at action 1132, the system sets the bit value ζ equal to false (logical 0). In either case, the bit value ζ is stored with its output coupled into an input of the two input logic gate 1140. After setting the bit at either of actions 1130,1132, the process continues to action 1133. At action 1133, a predetermined wait time (e.g., 0.1 seconds) elapses before the process loops back to action 1121 to repeat one or more of the actions 1121,1122,1124,11126,1128,1130,1132.

With the wait 1133 set to 0.1 seconds and the predetermined comparison number set to 10, the action 1128 generally causes a 1 second delay before the bit value ζ can be set to true and the valve V5 actuated to release vacuum in the accumulator during normal control and operation of the vacuum pump 704.

Logic gates 1140,1142 execute a logical function before the valve V5 is opened by a valve driver circuit 1138. With a logical AND gate, the system performs a logical AND operation 1140 on the bit value ζ with the vacuum pump state 1106. If the bit value ζ and the vacuum pump state 1106 are both true, the resultant output of the logical AND operation 1140 is true. Otherwise, if either the bit value ζ or the vacuum pump state 1106 are false, the resultant output of the logical AND operation 1140 is false. The system performs a logical OR operation 1142 on the result of the logical AND operation 1140 with the valve V5 state 1107. If either the result of the logical AND operation 1140 or the valve V5 state 1107 are true, the resultant output of the logical OR operation 1142 is true. Only if both the logical AND operation 1140 and the valve V5 state 1107 are false, is the resultant output of the logical OR operation 1142 false.

The valve driver circuit 1138 is coupled to the output of the OR gate to receive the result of the logical OR operation 1142 and control the valve V5.

At action 1136, a pressure transducer conditioning and PI (proportional-integral) feedback circuit generates an analog feedback error signal e in response to the differential pressure sensed by the pressure transducers TR2-TR1 (or the differential pressure transducer DPTR) across the flow channel of the flow cell. At action 1134, an ADC (analog-to-digital converter) receives the analog feedback error signal e and converts it into a digital feedback signal e that the firmware layer 1108A can digitally process. The digital feedback signal e is input to action 1120 to complete a feedback loop and have the cycle of actions continue. Other actions, processes, and/or details are discussed with reference to the figures and may be a part of the feedback control system and method 1100, depending on the implementation.

Figure 12:
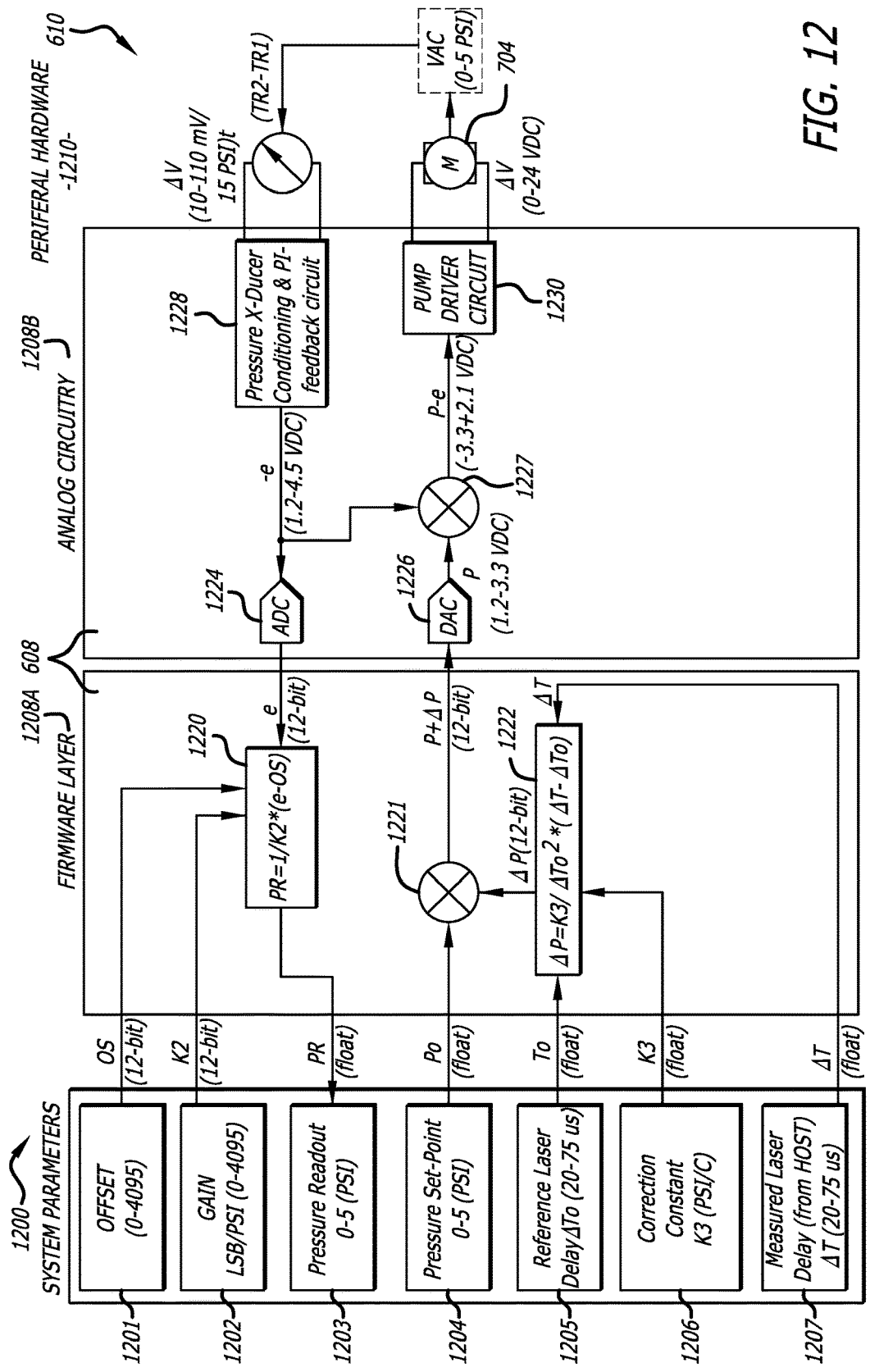
FIG. 12 is a flowchart for an example method to control vacuum pump feedback in the fluidics system.

Referring now to FIG. 12, a block diagram is shown of an example method and feedback control system 1200 to control the vacuum pump 704 in the fluidics system 604 illustrated in FIG. 7. In one embodiment, the acquisition system 608 includes a firmware layer 1208A and analog circuitry 1208B to carry out and provide the method and feedback control system 1200 to control the vacuum pump 704. The analysis system 610 interfaces with peripheral hardware 1210 to sense and control the vacuum pump motor to generate vacuum in a flow cytometry system. The peripheral hardware 1210 includes at least one pressure transducer (e.g., pressure transducer TR2 shown in FIG. 7) and the vacuum pump motor M 704.

Using the method and feedback control system 1200, the system generally drives the vacuum pump 704 to a pressure set-point and controls the core velocity flow in the flow cell 206 when there are changes. A pressure correction factor may be generated in response to an average measured time delay of particle flow between lasers (e.g., laser delay 1202) that is sensed by a pair of scattering channels. Particle velocity is inversely proportional to the time delay between lasers. If the time delay of a particle between lasers along the flow channel increases indicating a slower fluid and particle velocity, vacuum can be increased to increase core velocity flow and lower the particle time delay between lasers. If the time delay of a particle between lasers along the flow channel decreases indicating a faster fluid and particle velocity, the vacuum can be reduced to lower core velocity flow and increase the particle time delay between lasers. A pressure set-point 1204 is corrected in response to measured time delay between lasers before driving the vacuum pump 704.

The input system parameters include, without limitation, an offset 1201, a gain 1202, a pressure set-point 1204, a reference set-point 1205, a correction constant 1206, and a measured laser delay 1207. The output system parameters include a pressure readout 1203. The firmware layer 1208A includes a number of actions or processes and math logic that interface with the system parameters and the analog circuit 1208B. The analog circuitry 1208B includes a number of actions or processes and devices to interface with the firmware layer 1208A The analog circuitry 1208B includes a pressure transducer conditioning and PI (proportional-integral) feedback circuit that receives the differential pressure across transducers TR2-TR1 (or the differential pressure transducer DPTR). At action 1228, the pressure transducer conditioning and PI (proportional-integral) feedback circuit generates an analog feedback signal −e based on the voltages received from the differential pressure sensed by the transducers TR2-TR1.

At action 1224, an analog to digital converter (ADC) receives the analog feedback signal −e and converts it into a digital feedback signal −e for use by the digital logic and processes of the firmware layer 1208A.

At action 1220, a pressure calculating device receives the offset 1201, the gain 1202, and the digital feedback signal −e from the analog circuitry 1208B. The pressure calculating device calculates the pressure readout 1203 based on the offset 1201, the gain 1202, and the digital feedback signal −e.

At action 1222, a pressure correction calculator receives the reference laser delay 1205, the correction constant 1206, and the measured laser delay 1207. The pressure correction calculator calculates a differential pressure $\Delta P$, a correction factor that is based on the reference laser delay 1205, the correction constant 1206, and the measured laser delay 1207.

At action 1221, a summer or adder adds the pressure set point $P_0$ to the differential pressure $\Delta P$, forming a desired pressure value P. The output from the summer or adder, a digital value, is coupled into an analog-to-digital converter (ADC) 1226.

At action 1226, the ADC receives the digital value for the desired pressure value P from the summer or adder and converts into an analog value for the desired pressure P.

At action 1227, the system calculates a designated pressure (P−e) by adding or summing together the desired pressure P from the DAC and the negative feedback signal −e from the pressure transducer conditioning and PI (proportional-integral) feedback circuit 1228. The designated pressure (P−e) is coupled to a pump driver circuit.

At action 1230, the pump driver circuit receives the designated pressure (P−e) from the summer or adder 1227. The pump driver circuit is coupled to the vacuum pump motor 704. If the designated pressure starts to increase (less vacuum), the pump driver circuit may drive the vacuum pump motor 704 with a higher voltage to increase vacuum in the accumulator 702. If the designated pressure starts to decrease (more vacuum), the pump driver circuit may drive the vacuum pump motor 704 with a lower voltage to reduce vacuum in the accumulator 702.

The actions of the firmware layer 1208A and analog circuitry 1208B continually loop in a cycle of actions. Other actions, processes, and/or details are discussed with reference to the figures and may be a part of the method and system 1200, depending on the implementation.

CONCLUSION

A system, method, and apparatus for flow cytometry fluidics in a flow cytometer are described. In particular, a system is provided that includes dual laser devices and dual scatter channels to measure velocity of particles in a core stream of sample fluid. A first scatter channel detects a first light scatter generated by a particle passing through a first laser beam, wherein the particle flows in a sample fluid. A second scatter channel detects a second light scatter generated by the particle passing through a second laser beam, wherein the first laser beam and the second laser beam are separated by a distance (L). The system also includes a stepper motor modulated flow control valve to control the proportion of sheath flow rate and sample flow rate in a flow channel in a flow cell. The total flow rate of the sample fluid and the sheath fluid around the sample fluid is controlled, and thus held constant, by a feedback control system controlling a vacuum pump based on differential pressure across ends of a flow channel in the flow cell. In accordance with some embodiments, the stepper motor modulated flow control valve is a stepper motor modulated pinch valve.

When implemented in software, the elements of the embodiments of the invention are essentially the program, code segments, or instructions to perform the necessary tasks. The program, code segments, or instructions can be stored in a processor readable medium or storage device that can be read and executed by a processor. The processor readable medium may include any medium that can store information. Examples of the processor readable medium include, without limitation, an electronic circuit, a semiconductor memory device, a read only memory (ROM), a flash memory, an erasable programmable read only memory (EPROM), a floppy diskette, a CD-ROM, an optical disk, and a magnetic disk. The program or code segments may be downloaded via computer networks such as the Internet, Intranet, etc. and stored in the processor readable medium or storage device.

Some portions of the preceding detailed description may have been presented in terms of algorithms and symbolic representations that perform operations on data bits within a computer memory. These algorithmic descriptions and representations are the tools used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities may take the form of electrical (e.g., current or voltage) or magnetic signals capable of being stored, transferred, combined, compared, and otherwise manipulated. It has proven convenient at times, principally for reasons of common usage, to refer to these signals as bits, values, levels, elements, symbols, characters, terms, numbers, or the like.

However, all of these and similar terms are to be associated with the appropriate physical quantities and are merely convenient labels applied to these quantities. Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, processing logic, or similar electronic computing device, that automatically or semi-automatically manipulates and transforms data represented as physical (electronic) quantities within the computer system's registers and memories into other data similarly represented as physical quantities within the computer system memories or registers or other such information storage, transmission or display devices.

Additionally, the embodiments of the invention are not described with reference to any particular programming language. It will be appreciated that a variety of programming languages may be used to implement the teachings of the embodiments of the invention as described herein.

This disclosure contemplates other embodiments or purposes. It will be appreciated that the embodiments of the invention can be practiced by other means than that of the described embodiments, which are presented in this description for purposes of illustration and not of limitation. The specification and drawings are not intended to limit the exclusionary scope of this patent document. It is noted that various equivalents for the particular embodiments discussed in this description may be practiced by the claimed invention as well. That is, while specific embodiments of the invention have been described, it is evident that many alternatives, modifications, permutations and variations will become apparent in light of the foregoing description. Accordingly, it is intended that the claimed invention embrace all such alternatives, modifications and variations as fall within the scope of the appended claims. The fact that a product, process, or method exhibits differences from one or more of the described exemplary embodiments does not mean that the product or process is outside the scope (literal scope and/or other legally-recognized scope) of the following claims.

What is claimed is:

1. A flow cytometry system, comprising:
    a first scatter channel to detect a first light scatter generated by a particle passing through a first laser beam, wherein the particle flows in a flow channel of a sample fluid, wherein the first scatter channel generates first pulse information in response to detecting the first light scatter, the first pulse information including a first laser identifier and a first timestamp; and
    a second scatter channel to detect a second light scatter generated by the particle flowing in the flow channel of the fluid sample and passing through a second laser beam, wherein the first laser beam and the second laser beam are separated by a first predetermined distance.

2. The flow cytometry system of claim 1, wherein
    the first scatter channel and the second scatter channel are both side scatter channels, forward scatter channels, or off angle scatter channels.

3. The flow cytometry system of claim 1, wherein
    the first scatter channel is a forward scatter channel and the second scatter channel is a side scatter channel.

4. The flow cytometry system of claim 1, wherein
    the first scatter channel is a side scatter channel and the second scatter channel is a forward scatter channel.

5. The flow cytometry system of claim 1, further comprising:
    a first laser device at a first position in a flow channel to generate the first laser beam; and
    a second laser device at a second position in the flow channel to generate the second laser beam;
    wherein the first laser device and the second laser device are serially separated along a center axis of the flow channel by a second predetermined distance.

6. The flow cytometry system of claim 1, wherein
    the first predetermined distance is equivalent to the second predetermined distance.

7. The flow cytometry system of claim 1, further comprising:
    a flow cell to receive a flow of the sample fluid and a flow of a sheath fluid, wherein the flow of the sample fluid is surrounded by the flow of the sheath fluid.

8. The flow cytometry system of claim 7, further comprising:
    a flow control valve to control a volumetric ratio of the sheath fluid to the sample fluid.

9. The flow cytometry system of claim 8, wherein:
    a velocity of the flow of the sample fluid is proportional to the volumetric ratio of the sheath fluid to the sample fluid.

10. The flow cytometry system of claim 8, wherein:
    the flow control valve receives feedback associated with the velocity of the sample fluid; and the flow control valve adjusts a flow resistance of a path for the sheath fluid in response to the received feedback.

11. The flow cytometry system of claim 1, wherein:
the second scatter channel generates second pulse information in response to detecting the second light scatter, the second pulse information including a second laser identifier and a second timestamp.

12. The flow cytometry system of claim 11, further comprising:
an acquisition system to receive the first pulse information and the second pulse information.

13. The flow cytometry system of claim 12, wherein:
the acquisition system calculates a laser delay for the particle by calculating a time difference between the second timestamp and the first timestamp.

14. The flow cytometry system of claim 12, wherein:
the acquisition system includes a digital-to-analog converter (DAC) integrated in a field programmable gate array (FPGA).

15. The flow cytometry system of claim 1, further comprising:
a pressure release valve to regulate pressure in the flow cytometry system; and
an acquisition system to control the pressure release valve.

16. The flow cytometry system of claim 15, wherein the acquisition system:
receives a feedback signal associated with a pressure measurement in the flow cytometry system;
receives a pressure set-point and a pressure set-point tolerance; and
adjusts the pressure set-point in response to the feedback signal, the pressure set-point, and the pressure set-point tolerance.

17. The flow cytometry system of claim 1, further comprising:
a vacuum pump to regulate vacuum pressure in the system; and
an acquisition system to control the vacuum pump.

18. The flow cytometry system of claim 1, wherein the acquisition system:
receives a feedback signal associated with a pressure measurement in the flow cytometry system;
receives a pressure set-point, a reference laser delay, a correction constant, and a measured laser delay; and
calculates a designated pressure for the vacuum pump in response to the pressure set-point, the reference laser delay, the correction constant, and the measured laser delay.

* * * * *